(12) United States Patent
Zhao et al.

(10) Patent No.: US 10,710,594 B2
(45) Date of Patent: Jul. 14, 2020

(54) OCCUPANT-STATUS PREDICTION SYSTEM

(71) Applicant: Faurecia Automotive Seating, LLC, Auburn Hills, MI (US)

(72) Inventors: Ying (Carolyn) Zhao, Holland, MI (US); John M. Perraut, Rochester Hill, MI (US); Brian R. Dexter, Grand Haven, MI (US); James T. Hotary, Holland, MI (US); Matthew K. Benson, Holland, MI (US)

(73) Assignee: Faurecia Automotive Seating, LLC, Auburn Hills, MI (US)

(*) Notice: Subject to any disclaimer, the term of this patent is extended or adjusted under 35 U.S.C. 154(b) by 314 days.

(21) Appl. No.: 15/855,063

(22) Filed: Dec. 27, 2017

(65) Prior Publication Data
US 2018/0178808 A1 Jun. 28, 2018

Related U.S. Application Data

(60) Provisional application No. 62/439,550, filed on Dec. 28, 2016.

(51) Int. Cl.
*B60W 40/08* (2012.01)
*G01C 21/34* (2006.01)
(Continued)

(52) U.S. Cl.
CPC ............ *B60W 40/08* (2013.01); *B60N 2/002* (2013.01); *B60N 2/20* (2013.01); *B60N 2/90* (2018.02); *B60W 50/16* (2013.01); *G01C 21/34* (2013.01); *G05D 1/0061* (2013.01); *G08B 21/06* (2013.01); *A61B 5/024* (2013.01); *A61B 5/0205* (2013.01); *A61B 5/0816* (2013.01); *A61B 5/1103* (2013.01); *A61B 5/1114* (2013.01); *A61B 5/1116* (2013.01); *A61B 5/1118* (2013.01); *A61B 5/1128* (2013.01); *A61B 5/163* (2017.08); *A61B 5/18* (2013.01); *A61B 5/4806* (2013.01); *A61B 2560/0247* (2013.01); *B60W 2040/0827* (2013.01); *B60W 2040/0872* (2013.01);
(Continued)

(58) Field of Classification Search
CPC .......... B60W 40/08; G01C 21/34; G05D 1/00
See application file for complete search history.

(56) References Cited

U.S. PATENT DOCUMENTS 9,402,577 B2 8/2016 Ko
9,507,413 B2 11/2016 Gee
(Continued)

FOREIGN PATENT DOCUMENTS

DE 102009046913 5/2011
DE 102012112802 6/2014
(Continued)

OTHER PUBLICATIONS

Extended European Search Report for European App. No. 17210624.7 dated Apr. 17, 2018, 5 pages.

*Primary Examiner* — Kira Nguyen
(74) *Attorney, Agent, or Firm* — Barnes & Thornburg LLP

(57) ABSTRACT

An occupant support adapted for use in a vehicle includes a seat bottom, a seat back, and a sensory system. The seat bottom is coupled to a floor of the vehicle. The seat back extends upwardly away from the seat bottom. The sensor system is configured to monitor for fatigue of an occupant of the occupant support.

16 Claims, 19 Drawing Sheets

(51) Int. Cl.
    *G05D 1/00*     (2006.01)
    *B60W 50/16*     (2020.01)
    *B60N 2/90*     (2018.01)
    *G08B 21/06*     (2006.01)
    *B60N 2/00*     (2006.01)
    *B60N 2/20*     (2006.01)
    *A61B 5/11*     (2006.01)
    *A61B 5/18*     (2006.01)
    *A61B 5/16*     (2006.01)
    *A61B 5/00*     (2006.01)
    *A61B 5/0205*     (2006.01)
    *A61B 5/024*     (2006.01)
    *A61B 5/08*     (2006.01)
(52) U.S. Cl.
    CPC ..... *B60W 2420/10* (2013.01); *B60W 2420/42* (2013.01); *B60W 2530/00* (2013.01); *B60W 2540/043* (2020.02); *B60W 2540/22* (2013.01); *B60W 2554/00* (2020.02)

(56) References Cited

U.S. PATENT DOCUMENTS

| | | | |
|---|---|---|---|
| 10,241,509 B1* | 3/2019 | Fields | A61B 5/4094 |
| 2015/0142244 A1* | 5/2015 | You | G05D 1/0061 |
| | | | 701/23 |
| 2016/0092825 A1 | 3/2016 | Zimmer | |
| 2016/0280230 A1* | 9/2016 | Hsieh | B60Q 9/00 |
| 2017/0090475 A1* | 3/2017 | Choi | A61B 5/0488 |
| 2017/0327124 A1* | 11/2017 | Kim | B60N 2/002 |
| 2017/0355377 A1* | 12/2017 | Vijaya Kumar | B60W 40/08 |
| 2018/0118219 A1* | 5/2018 | Hiei | B60W 40/09 |

FOREIGN PATENT DOCUMENTS

| | | |
|---|---|---|
| DE | 102014203922 | 9/2015 |
| JP | 1918892 A1 | 5/2008 |
| JP | 2010146209 | 7/2010 |
| KR | 1020140147233 | 12/2014 |
| WO | 2014167811 | 10/2014 |

* cited by examiner

- LONG-RANGE RADAR
- LIDAR
- CAMERA
- SHORT-/MEDIUM-RANGE RADAR

| SLEEP SCORE = GREEN | TASK SCORE = GREEN | TASK SCORE = YELLOW | TASK SCORE = RED |
|---|---|---|---|
| BIOMETRICS = GREEN | FATIGUE MONITORING MODE | FATIGUE PREVENTION MODE | FATIGUE PREVENTION MODE |
| BIOMETRICS = YELLOW | FATIGUE PREVENTION MODE | FATIGUE PREVENTION MODE | FATIGUE MITIGATION MODE |
| BIOMETRICS = RED | WARNING | WARNING | STOP |

350

| SLEEP SCORE = YELLOW | TASK SCORE = GREEN | TASK SCORE = YELLOW | TASK SCORE = RED |
|---|---|---|---|
| BIOMETRICS = GREEN | FATIGUE MONITORING MODE | FATIGUE PREVENTION MODE | FATIGUE PREVENTION MODE |
| BIOMETRICS = YELLOW | FATIGUE PREVENTION MODE | FATIGUE MITIGATION MODE | WARNING |
| BIOMETRICS = RED | WARNING | STOP | STOP |

360

| SLEEP SCORE = RED | TASK SCORE = GREEN | TASK SCORE = YELLOW | TASK SCORE = RED |
|---|---|---|---|
| BIOMETRICS = GREEN | FATIGUE MONITORING MODE | FATIGUE PREVENTION MODE | FATIGUE PREVENTION MODE |
| BIOMETRICS = YELLOW | FATIGUE MITIGATION MODE | WARNING | WARNING |
| BIOMETRICS = RED | STOP | STOP | STOP |

OCCUPANT-STATUS PREDICTION SYSTEM

PRIORITY CLAIM

This application claims priority under 35 U.S.C. § 119(e) to U.S. Provisional Application Ser. No. 62/439,550, filed Dec. 28, 2016, which is expressly incorporated by reference herein.

BACKGROUND

The present disclosure relates to occupant supports including sensors. More particularly, the present disclosure relates to occupant supports for use in a vehicle and including one or more sensors configured to monitor an occupant of the occupant support while the vehicle is in use.

SUMMARY

According to the present disclosure, an occupant support system in accordance with the present disclosure is adapted for use in a vehicle. The occupant support system includes a seat bottom and a seat back. The seat back is coupled to the seat bottom and arranged to extend in an upward direction away from the seat bottom.

In illustrative embodiments, the occupant support system is configured to predict when an occupant of the occupant support system is experiencing fatigue. The occupant support system includes a sensor system and a control system. The sensor system is configured to obtain biometrics input, sleep input, and vehicle input. The control system is configured to determine a biometrics score, a sleep score, and a task score based on the biometrics input, sleep input, and vehicle input, respectively. The control system determines the occupant fatigue based on the biometrics score, sleep score, and task score.

In illustrative embodiments, the control system is configured to activate a vehicle system included in the vehicle to minimize occupant fatigue. The vehicle system may include massage systems, lighting systems, aroma systems, sound systems, etc. The vehicle systems may include a display and the control system generates instructions to provide a suggested travel route to the occupant through the display to minimize fatigue.

In illustrative embodiments, the control system and sensor system continue to monitor the occupant and the vehicle systems to determine the effect of activating the vehicle systems to learn which therapies are most effective as well as the occupant's preferences. The occupant data, scores, and learned occupant behaviors are associated in a unique occupant data profile associated with a single occupant. The control system adds information and trends to the unique occupant data profile over time to improve its occupant comfort and wellness recommendations.

In illustrative embodiments, the sleep input includes one or more of a number of hours that the occupant has been without sleep, a sleep history, and circadian information. The vehicle input includes one or more of traffic information, a level of carbon dioxide in a cabin of the vehicle, a light level in the cabin of the vehicle, a noise level in the cabin, and vibration of the occupant support. The biometrics input includes one or more of heart rate of the occupant, a respiration rate of the occupant, an eye blink rate of the occupant, a head position of the occupant, a posture of the occupant, focus of the occupant, eye direction of the occupant, hand position of the occupant, and sweat and skin temperature of the occupant.

Additional features of the present disclosure will become apparent to those skilled in the art upon consideration of illustrative embodiments exemplifying the best mode of carrying out the disclosure as presently perceived.

BRIEF DESCRIPTION OF THE DRAWINGS

The detailed description particularly refers to the accompanying figures in which:

FIG. 26 is a diagrammatic view showing a plurality of mode outcomes of the occupant support system based on weighing the sleep score, task score, and biometrics score of the occupant.

DETAILED DESCRIPTION

Figure 1:
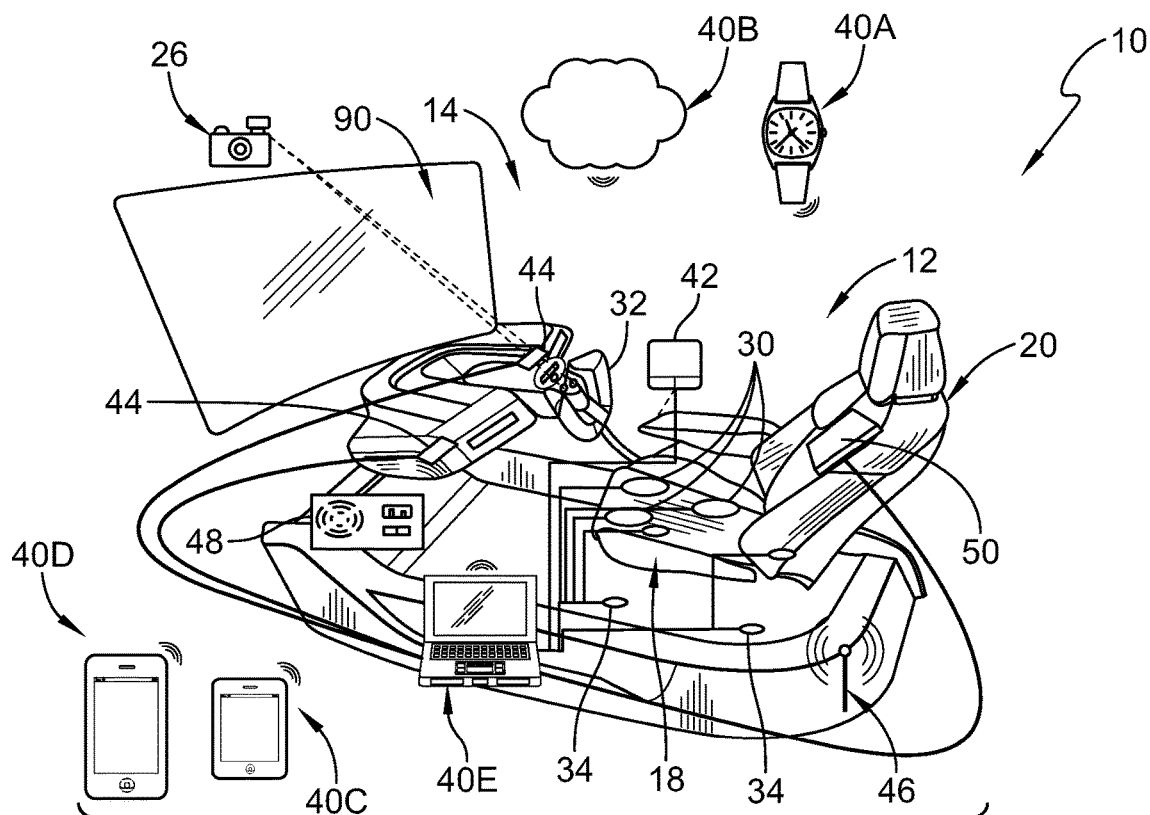
FIG. 1 is a perspective and diagrammatic view of an occupant support system in accordance with the present disclosure showing that the occupant support system is adapted for use in a vehicle and that the occupant support system includes a sensor system including a plurality of sensors configured to measure physiological, behavioral, and sleep data of an occupant of the occupant support system and to obtain vehicle data and data relating to an environment around and within the vehicle.
Figure 5:
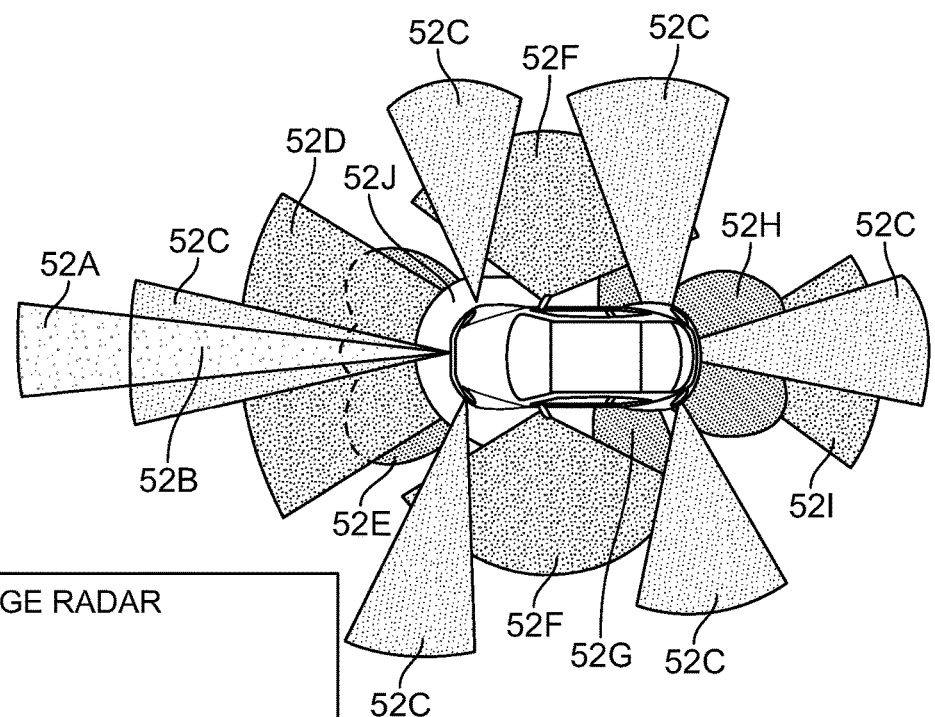
FIG. 5 is a top plan and diagrammatic view of a vehicle adapted to include the occupant support system and showing that the sensor system included in the occupant support system further includes a long-range radar, a LIDAR system, an optical camera, and a short-/medium-range radar.
Figure 6:
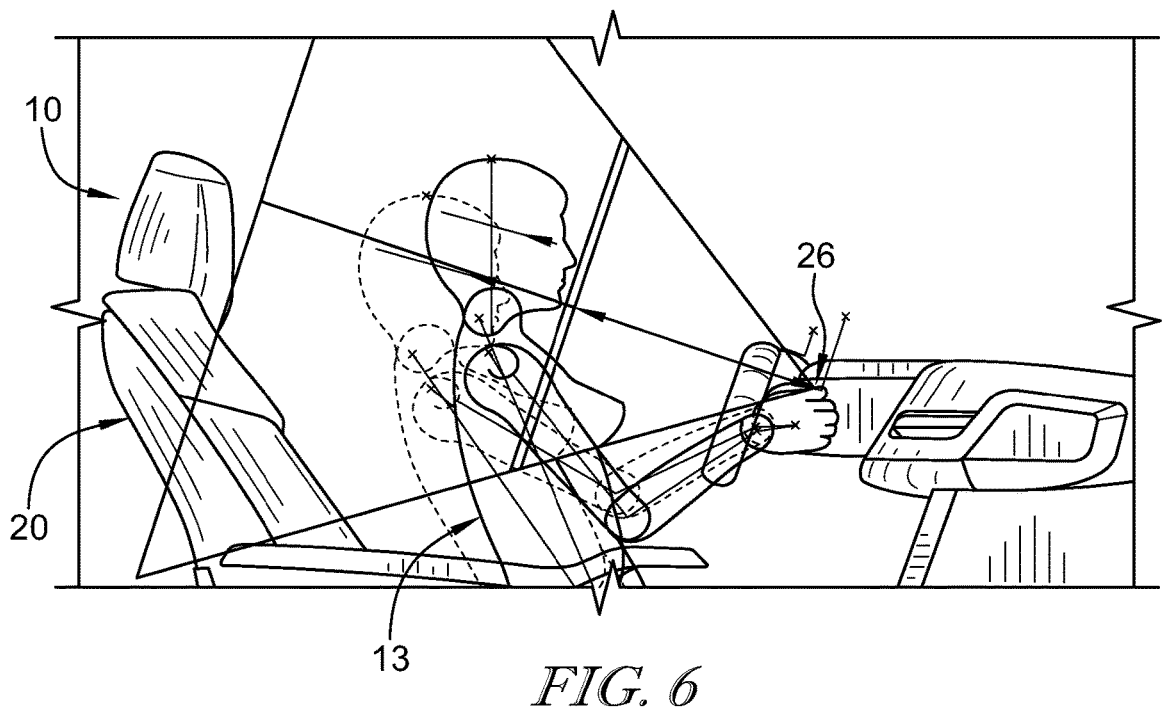
FIG. 6 is a diagrammatic view of the occupant support system of FIG. 1 showing an occupant positioned near the optical camera system included in the sensor system and suggesting that the optical camera system is configured to view the occupant's face and shoulders and further configured to focus on the occupant when the occupant is in different sitting arrangements and distances relative to the optical camera system.

An occupant support system 10 in accordance with the present disclosure is adapted for use in a vehicle 11 as shown in FIGS. 1, 5, and 6. Occupant support system 10 is configured to support an occupant 13 in vehicle 11 and to monitor health and behavior characteristics of occupant 13 to generate recommendations to improve occupant's wellness and/or comfort. For example, occupant support system 10 may recommend activating a massage system 86 to improve occupant's comfort and blood flow or recommend a coffee break if occupant 13 is likely to be drowsy. Over time, occupant support system 10 obtains more and more occupant health data and occupant feedback to improve its recommendations and, thereby, improve occupant wellness and/or comfort.

Figure 2:
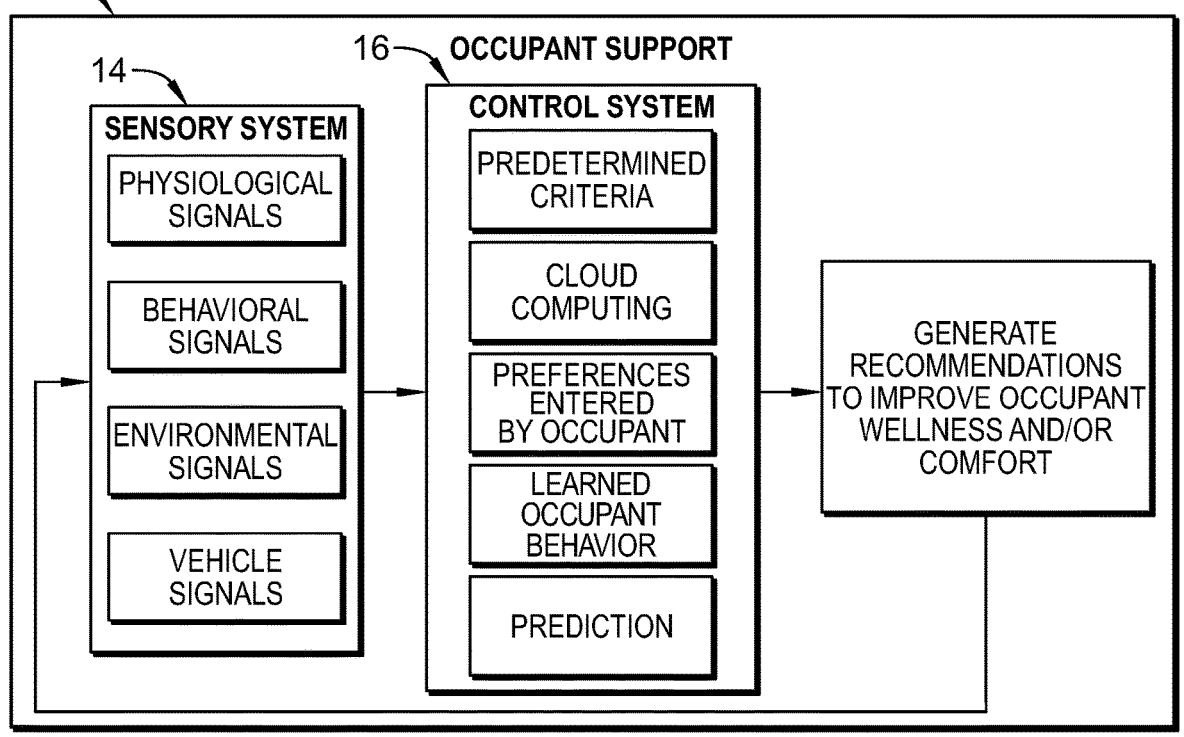
FIG. 2 is a diagrammatic view of the occupant support system of FIG. 1 showing that the occupant support system includes the sensor system and a control system, the sensor system is configured to detect one or more of occupant physiological signals, occupant behavioral signals, sleep signals, environmental signals, and vehicle signals, and the control system is configured to analyze the signals to generate occupant health data, occupant state data such as fatigue, and recommendations to improve a wellness and/or comfort of the occupant based on the occupant health data and/or the occupant state data.

Occupant support system 10 includes a seat 12, a sensor system 14, and a control system 16 as shown in FIGS. 1 and 2. Seat 12 includes a seat bottom 18 coupled to a floor of vehicle 11 and a seat back 20 that extends upwardly away from seat bottom 18. Sensor system 14 includes a plurality of sensors configured to measure occupant physiology, occupant behavior, surrounding environment information, and vehicle information as suggested in FIGS. 3-8. Control system 16 determines occupant health data indicative of physiological and behavioral characteristics of occupant 13 and occupant state data indicative of a state of occupant 13 based on the signals from sensor system 14 as suggested in FIG. 11A. Control system 16 analyzes the occupant health data and occupant state data and determines recommendations for improving the wellness and/or comfort of occupant 13 as suggested in FIG. 11B.

Based on at least one of the occupant health data and the occupant state data, control system 16 identifies one or more of a plurality of vehicle systems 78 suitable to change at least one physiological characteristic or behavioral characteristic of occupant 13. For example, control system 16 may determine that a sound system 80 is suitable for changing a heart rate 102 of occupant 13. Control system 16 recommends to occupant 13 to activate the vehicle system(s) 78 based on the occupant health data and the occupant state data.

Vehicle system 78 may be activated automatically by control system 16 or manually by occupant 13 in response to the recommendation. Alternatively, occupant 13 may activate a different vehicle system 78. Control system 16 monitors which vehicle system(s) 78 is activated and the effect on the occupant health data and occupant state data. Control system 16 associates the selected vehicle system 78, the occupant health data, and the occupant state data in a unique occupant data profile to learn occupant preferences and effective recommendations. Future recommendations may be based on the occupant's preferences and effective recommendations such that they are more tailored to occupant 13 over time.

Recommendations may also include external activities and therapies. For example, control system 16 may determine that occupant 13 is or will likely be drowsy and recommend a coffee break. In another example, control system 16 is aware of a medication schedule of occupant 13 and recommends taking the medication at a scheduled time.

Control system 10 determines a health score of occupant 13 in some embodiments. The health score is determined based on one or more of the occupant health data, occupant state data, and medical conditions known to control system 16. Control system 16 is configured to display the health score for occupant's information as suggested in FIG. 11C. In one example, the health score is normalized by comparing it with health scores of occupants of other vehicles through cloud computing.

Advanced analytics may be used for identifying correlations between occupant 13 and the events experienced to suggest action using recommendations. Suggested actions result from advanced analytics of similar occupant profiles on the cloud with similar situational data, for example a pool of participant data that has already experienced the situation this particular occupant is experiencing, to make recommendations to this particular occupant 13 in some embodiments.

Occupant support system 10 includes seat 12, sensor system 14, and control system 16 as shown in FIGS. 1 and 2. Seat 12 is configured to support occupant 13 in vehicle 11. Sensor system 14 measures occupant physiology, occupant behavior, surrounding environment information, and vehicle information. Control system 16 analyzes the signals and determines recommendations for improving the wellness and/or comfort of occupant 13 based on the analyzed signals.

Seat 12 includes seat bottom 18 and seat back 20 as shown in FIG. 1. Seat bottom 18 is configured to move relative to the floor of the vehicle. Seat back 20 is configured to move relative to seat bottom 18 such that seat 12 is configured to move between an upright position and a folded-forward position. Seat 12 includes a plurality of sensors included in sensor system 14. In the illustrative embodiment, seat 12 is a driver side seat 12.

Sensor system 14 includes the plurality of sensors as shown in FIGS. 3-10. Measurements from sensor system 14 are used to determine occupant health data and occupant state data as suggested in FIG. 3.

Figure 3:
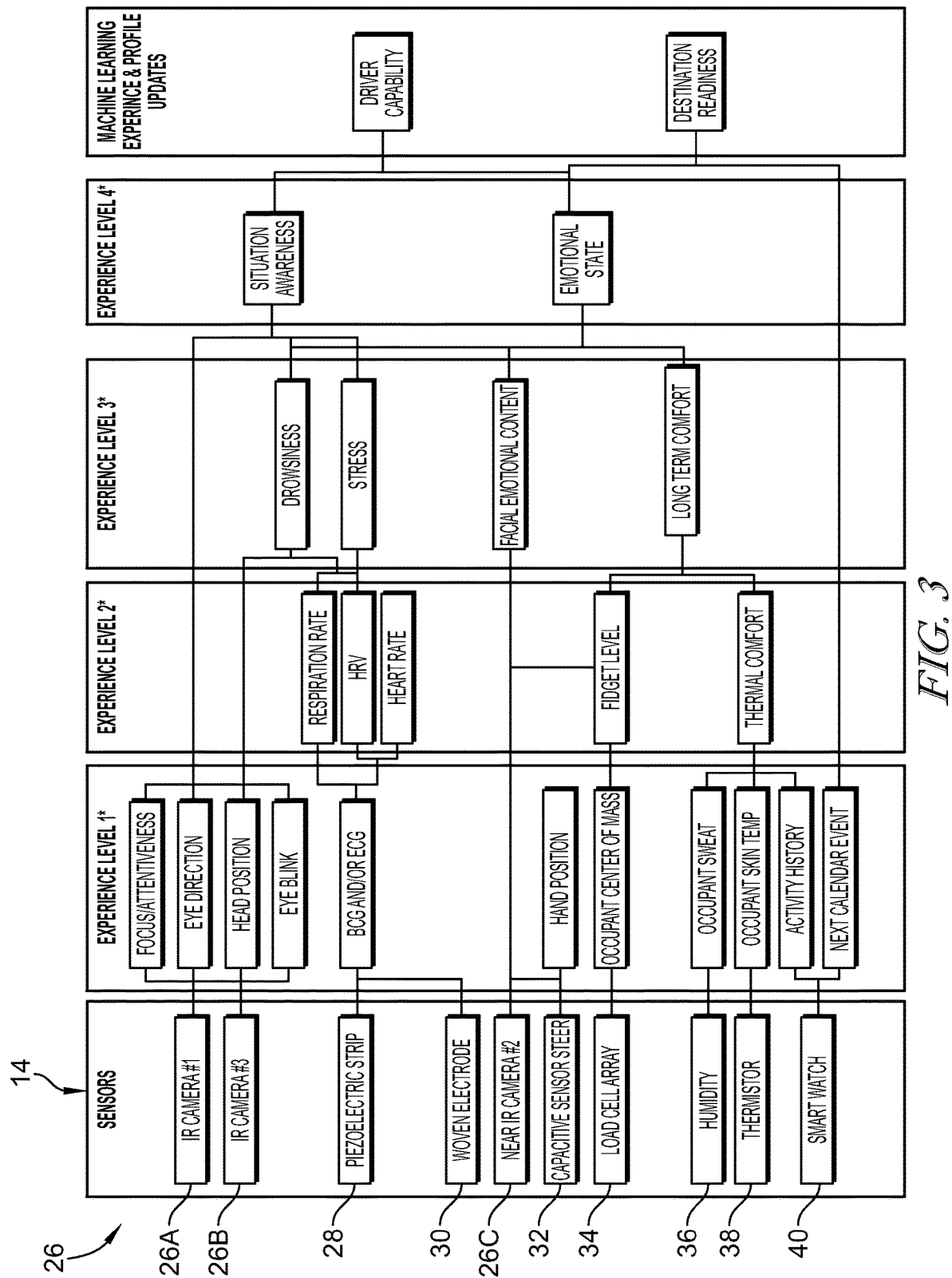
FIG. 3 is a diagrammatic view of the sensor system included in the occupant support system suggesting a plurality of biometrics input that can be measured by the sensor system and showing experience levels of the occupant that may be determined by the control system based on the signals received from the sensor system.
Figure 4:
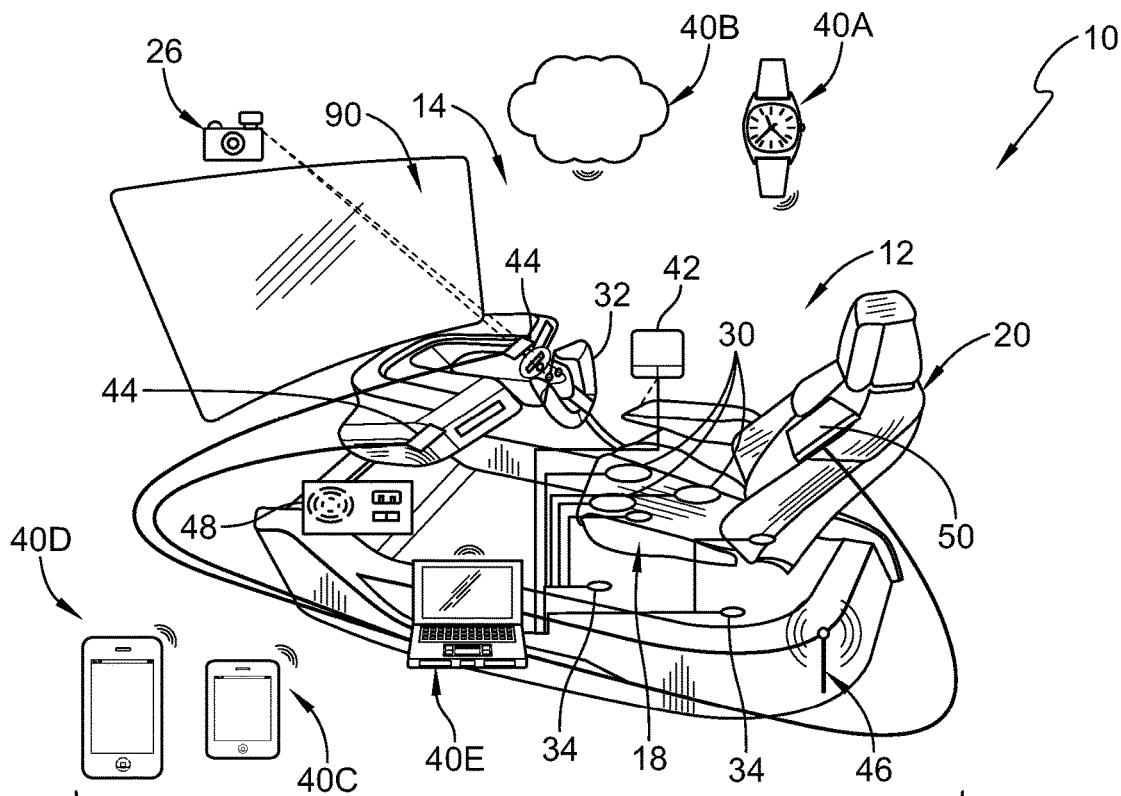
FIG. 4 is a perspective and diagrammatic view of the occupant support system similar to FIG. 1 showing that the sensor system included in the occupant support system includes a plurality of sensors for measuring physiological, behavioral, sleep, vehicle, and environmental signals, the sensor system including an optical camera system, cloud analytics, external input devices such as a smart watch, smart phone, and tablet, a control board, a touch pad, an infrared emitter, an electrode, a piezoelectric sensor, a humidity sensor, a temperature sensor, a capacitive sensor, a load cell, and an oximetry sensor.

Sensor system 14 includes optical camera system 26, a piezoelectric sensor 28, an electrode 30 (i.e. woven electrode), a capacitive sensor 32, a load cell(s) 34, a humidity sensor 36, a thermistor 38, and smart devices 40 such as, for example, a smart watch 40A, cloud computing 40B, a smart phone 40C, a tablet 40D, and a personal computer 40E as shown in FIGS. 3 and 4. Thermistor 38 is configured to detect occupant temperature, cabin temperature, and outside temperature. Smart devices 40 communicate with occupant support system 10 via Bluetooth in some embodiments and may provide data in real-time when occupant 13 sits in occupant support system 10. Sensor system 14 further includes touch pad 42, control board 44 input devices, an accelerometer, a volatile organic compound sensor, an electrically-activated polymer sensor, and an air particulate sensor.

Sensor system 14 further includes a plurality of vehicle and environmental sensors 52 as shown in FIG. 5. Vehicle and environmental sensors 52 include a long-range RADAR, LIDAR, an optical camera, and short-/medium-range RADAR. Vehicle and environmental sensors 52 include vehicle to vehicle communication devices and vehicle to infrastructure communication devices in some embodiments.

A plurality of zones can be sensed with the vehicle and environmental sensors 52 as suggested in FIG. 5. The zones may include for example, an adaptive cruise control zone 52A; emergency braking, pedestrian detection, and collision avoidance zone 52B; environment mapping zones 52C; traffic sign recognition and lane departure warning zone 52D; traffic alert zone 52E; digital side mirror and surround view zones 52F; blind spot detection zone 52G; rear collision detection zone 52H; park assist, surround view, and rear view mirror zone 52I; and park assist zone 52J.

Figure 8:
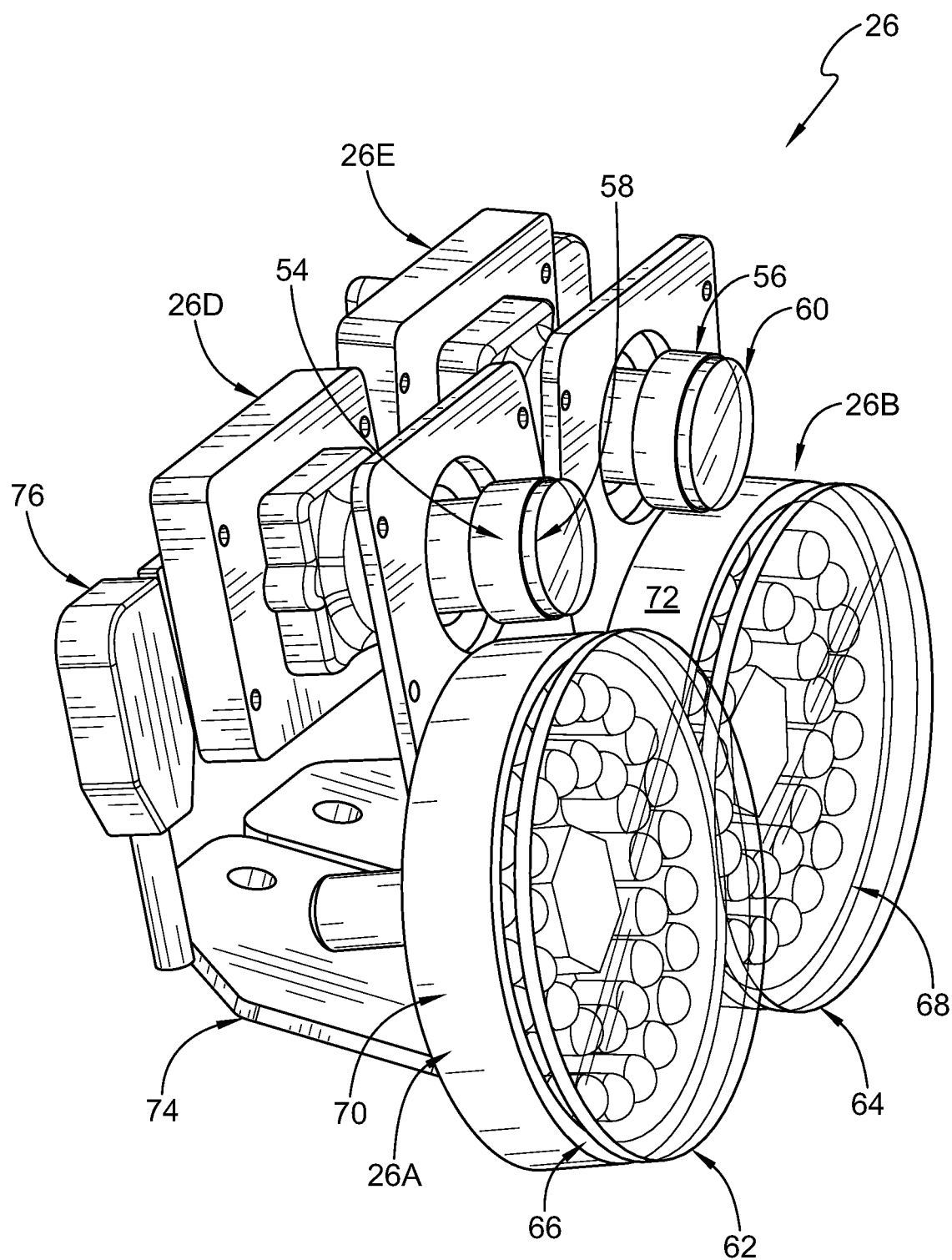
FIG. 8 is a perspective view of the optical camera system included in the sensor system showing that the optical camera system includes a first visible light camera, a second visible light camera, a first infrared camera, and a second infrared camera.

Optical camera system 26 of sensor system 14 include a first infra-red camera 26A, a second infrared camera 26B, a third infrared camera 26C, a first visible light camera 26D, and a second visible light camera 26E as shown in FIGS. 3, 4, and 8. Infrared cameras 26A, 26B, 26C include near-field and far-field infrared cameras. In some embodiments, sensor system 14 further includes a fluid pressure sensor. As shown in FIG. 4, occupant support system 10 further includes a wireless router 46, a power supply 48, and an electronic control unit 50.

Figure 7:
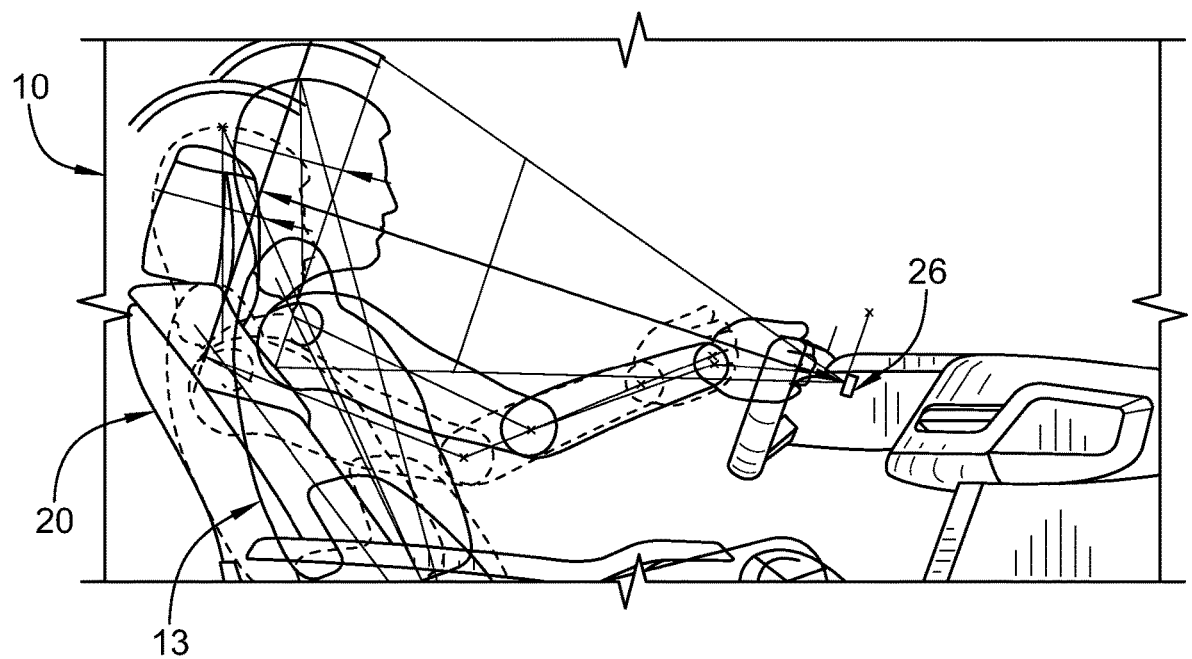
FIG. 7 is a view similar to FIG. 6 showing that the occupant is positioned far away from the optical camera system included in the sensor system and suggesting that the optical camera system is configured to view the occupant's face and shoulders.

Optical camera system 26 is configured to change a field of view to detect occupant 13 when occupant 13 is in a plurality of positions as suggested in FIGS. 6 and 7. In one example, optical camera system 26 uses a camera with a 3.6 millimeter diameter lens 54 to view occupant 13 as little as about 350 millimeters away from optical camera 26 with a field of view of about 69 degrees as suggested in FIG. 6. Optical camera system 26 further includes a camera with an 8.0 millimeter diameter lens 56 to view occupant 13 as far as about 850 millimeters away from optical camera 26 with a field of view of about 34 degrees as suggested in FIG. 7.

One embodiment of optical camera system 26 is shown in FIG. 8. Optical camera system 26 is located in a steering column of vehicle 11 as suggested in FIG. 4. Optical camera system 26 includes first visible light camera 26D, second visible light camera 26E, first infra-red camera 26A, and second infrared camera 26B. Each visible light cameras 26D, 26E include a lens 54, 56 and a filter 58, 60 respectively. Lens 54 is a 3.6 millimeter lens and lens 56 is an 8.0 millimeter lens. Infra-red cameras 26A, 26B include diffusers 62, 64 filters 66, 68, and guides 70, 72 respectively. Optical camera system 26 further includes a mount 74 and a USB port 76.

Figure 9:
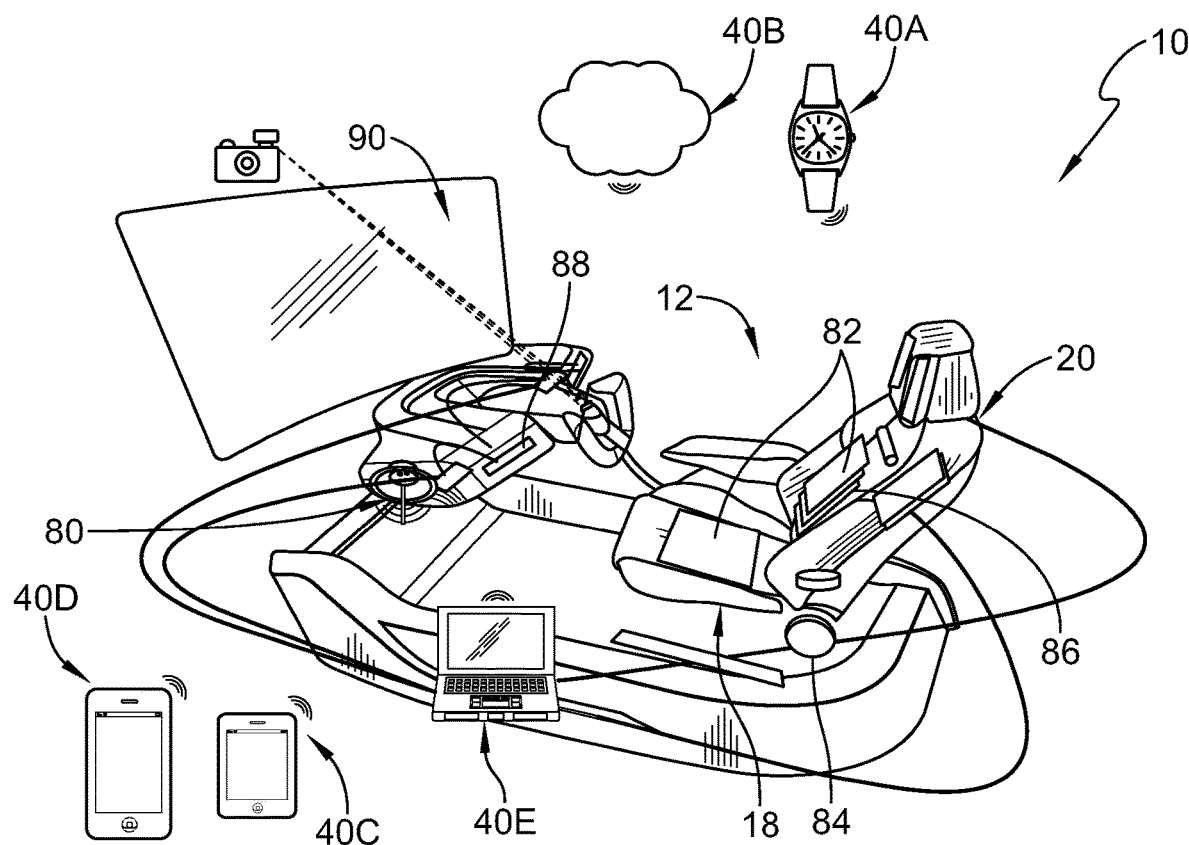
FIG. 9 is view similar to FIG. 1 showing that the occupant support system includes a plurality of vehicle systems adapted to provide informational, tactile, visual, aural, olfactory, and thermal feedback to the occupant to provide health information and/or therapies for the occupant.
Figure 10:
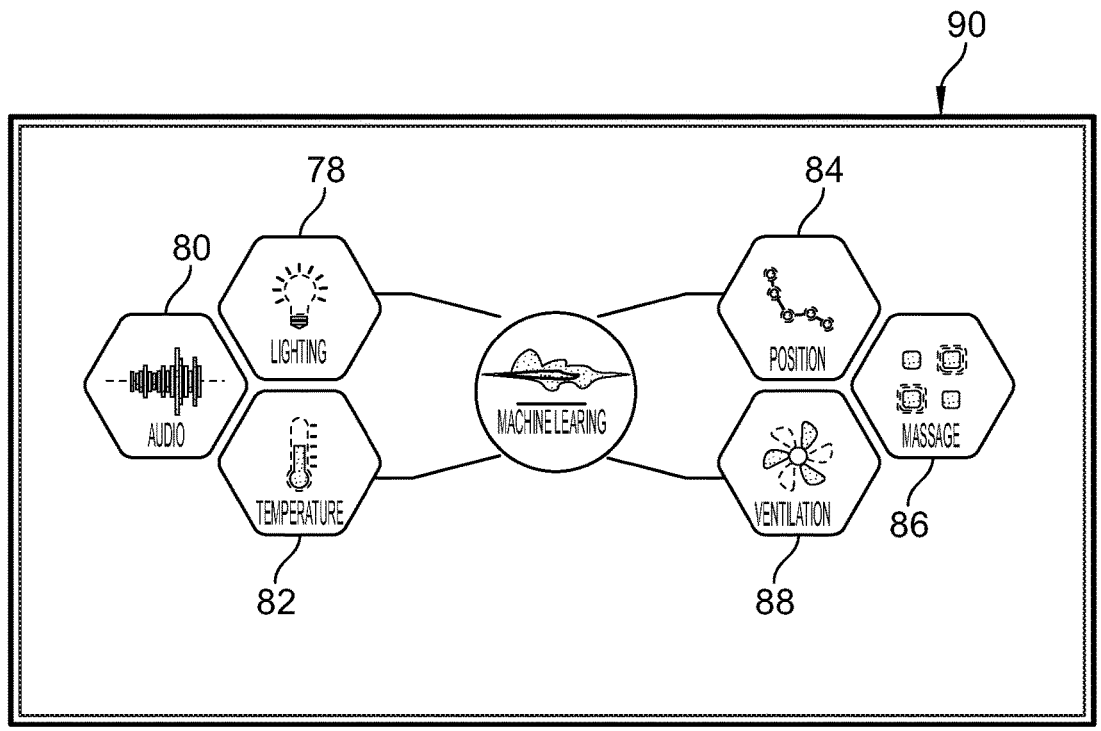
FIG. 10 is a diagrammatic view of a display included in the occupant support system showing that the vehicle systems included in the occupant support system include an audio system, a lighting system, a temperature system, an occupant position system, a ventilation system, and a massage system.

Occupant support system 10 includes a plurality of vehicle systems 78 (sometimes called outputs) as shown in FIGS. 9 and 10. Vehicle systems 78 provide informational, tactile, visual, audial, olfactory, and thermal feedback to occupant 13. Vehicle systems 78, alone or in combination, may be activated to apply a variety of therapies to occupant 13 to change at least one physiological characteristic or behavioral characteristic of occupant 13.

Vehicle systems 78 include a lighting system 81, an audio sound system 80, a temperature system 82, a position system 84, a massage system 86, a ventilation system 88, a visual display 90, smart devices 40A, 40B, 40C, 40D, 40E, and optical camera system 26 as shown in FIGS. 9 and 10. Position system 84 includes adjustable seat bottom 18 and adjustable seat back 20. Temperature system 82 includes a heating and/or cooling system included in seat 12.

Figure 11A:
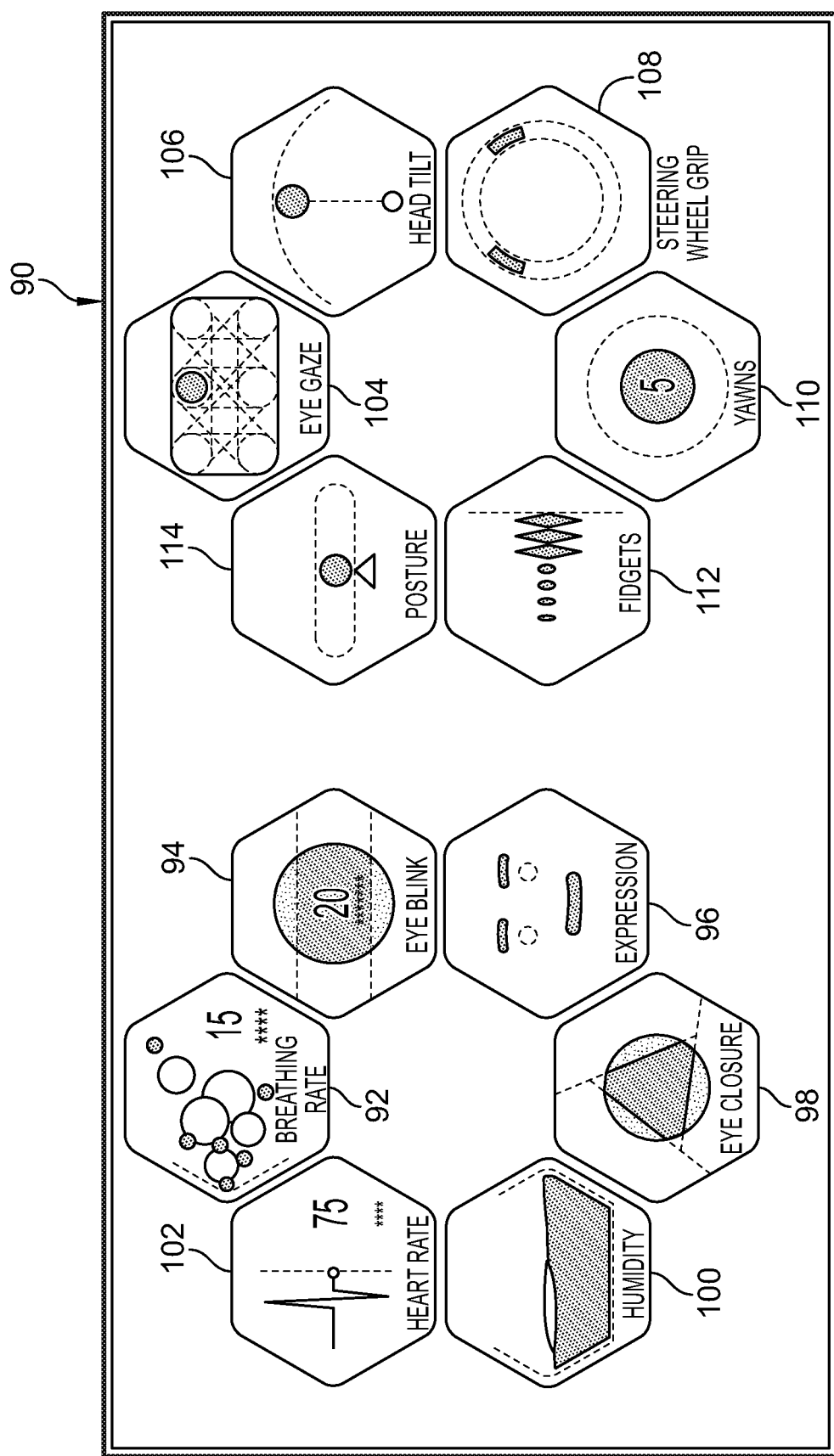
FIG. 11A is a diagrammatic view of the display included in the occupant support system showing occupant health data indicative of physiological and behavioral characteristics of the occupant.
Figure 11B:
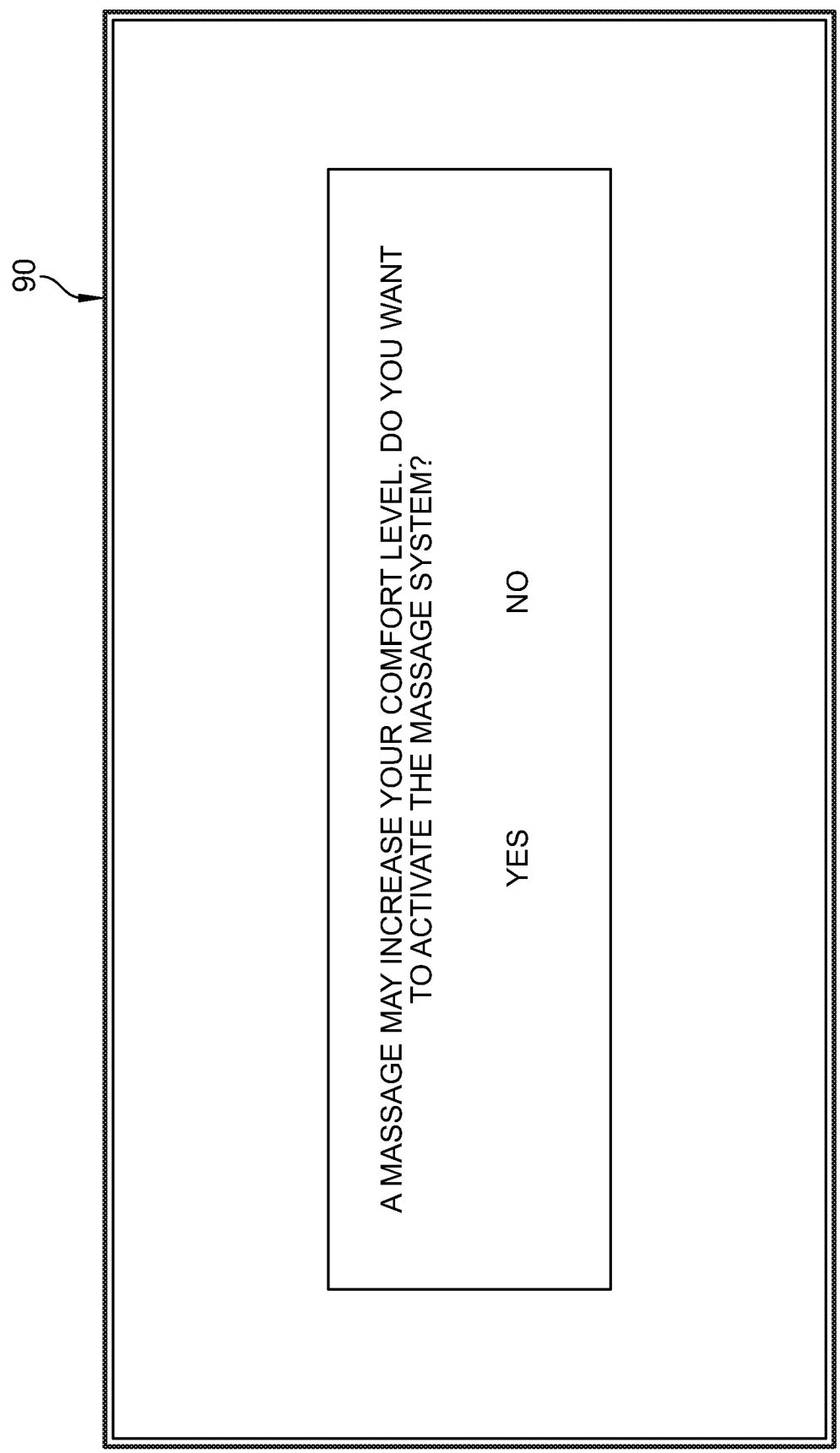
FIG. 11B is a diagrammatic view of the display included in the occupant support system showing that the occupant support system recommends activating vehicle systems to improve occupant wellness or comfort.

Control system 16 determines occupant health data and occupant state data based on the signals generated by sensor system 14 as suggested in FIGS. 3 and 11A. Control system 16 determines data based on different experience levels as shown in FIG. 3. Occupant health data and occupant state data are provided in real-time. FIG. 3 provides one example of the signals and data used to determine the data of experience levels 1-4 and the machine learning and profile update level. Other examples of determining data based on different signals and data are within the scope of this disclosure and a number of examples are provided herein.

Control system 16 is configured to determine occupant focus, occupant eye direction, occupant head position, an eye blink rate 94 of occupant 13, a BCG or ECG (electrocardiogram) of occupant 13, a hand position of occupant 13, a center of mass of occupant 13, occupant sweat level, occupant skin temperature, an activity history of occupant 13, and a next calendar event of occupant 13 in experience level 1. Occupant focus, occupant eye direction, occupant head position, and the eye blink rate 94 of occupant 13 are determined based on signals from the optical camera system 26. BCG or ECG (electrocardiogram) of occupant 13 is determined based on signals from the piezoelectric sensor 28 and the electrode 30. The hand position of occupant 13 is based on signals from the capacitive sensor 32 which determines steering wheel grasp. The center of mass of occupant 13 is based on signals from the load cell(s) 34. The occupant sweat level is based on signals from the humidity sensor 36. The occupant skin temperature is based on signals from the thermistor 38. The activity history of occupant 13 and a next calendar event of occupant 13 are based on signals from the smart devices 40.

A respiration rate of occupant 13, heart rate variation (HRV), and heart rate 102 of occupant 13 are based on the ECG data determined in level 1 as shown in FIG. 3. Fidget level 112 of occupant 13 is based on signals from optical camera system 26 and capacitive sensor 32 as well as occupant center of mass data determined in experience level 1. The thermal comfort of occupant 13 is based on occupant sweat level, occupant skin temperature, and activity history data determined in experience level 1.

A drowsiness of occupant 13, stress of occupant 13, facial emotional content of occupant 13, and long term comfort of occupant 13 are determined in experience level 3 as shown in FIG. 3. Drowsiness of occupant 13 is based on one or more of focus of occupant 13, eye direction of occupant 13, head position of occupant 13, eye blink rate 94 of occupant 13, respiration rate of occupant 13, and HRV of occupant 13 determined in experience levels 1 and 2. Stress of occupant 13 is based on respiration rate and HRV data determined in experience level 2. The facial emotional content of occupant 13 is based on signals from optical camera system 26 and fidget level data determined in experience level 2.

Long term comfort of occupant 13 is based on fidget level 112 and thermal comfort data determined in experience level 2. Hand and leg position feed into facial content, fidget level 112, thermal comfort, long-term comfort, and emotional state. Biometric and/or wearables including smart devices 40 include activity history with feedback from sweat and skin temperature experiences, with a next calendar event connection to devices 40.

A situational awareness of occupant 13 and an emotional state of occupant 13 are determined in experience level 4 as shown in FIG. 3. Situational awareness of occupant 13 is determined based on one or more of focus of occupant 13, eye direction 104 of occupant 13, head position 106 of occupant 13, eye blink rate 94 of occupant 13, respiration rate of occupant 13, drowsiness, stress, facial emotional content, and long term comfort data determined in experience levels 1, 2, and 3. Emotional state of occupant 13 is based on one or more of drowsiness, stress, facial emotional content, and long term comfort of occupant 13 data determined in experience level 3.

Machine learning experience level and profile updates includes driver capability and destination readiness as shown in FIG. 3. Driver capability is based on situation awareness and emotional state data determined in experience level 4. Destination readiness is based on emotional state and next calendar event data determined in experience levels 1 and 4.

In the illustrative embodiment, control system 16 is configured to generate instructions to display occupant health data, for example, on display 90 for occupant information as suggested in FIG. 11A. The occupant health data is displayed in geometric patterns and includes indicia of the health data and numeric values or graphical values associated with the occupant health data. Breathing rate 92, eye blink rate 94, the facial expression 96, eye closure level 98, humidity 100 around occupant 13, heart rate 102, eye gaze 104, head tilt 106, steering wheel grip 108, yawn rate 110, fidget level 112, and posture 114 of occupant 13 are displayed in FIG. 11A.

Control system 16 is configured to determine occupant state data based on the occupant health data and generate instructions to display the occupant health data to occupant 13 as suggested in FIGS. 12-16. A plurality of states are shown and described, however other occupant states are contemplated. Occupant state data includes numerical values indicative of the severity of the state in some embodiments. In some embodiments, occupant state data is determined to be normal, low, or high based on predetermined criteria.

Control system 16 is configured to receive the occupant-body signals and the behavioral signals from sensor system 14 and determine occupant health data indicative of physiological characteristics and behavioral characteristics of occupant 13 based on the occupant-body signals and the behavioral signals. Control system 16 further determines occupant state data indicative of a state of occupant 13 based on the occupant health data.

Control system 16 identifies a vehicle system 78 configured to change at least one physiological characteristic or behavioral characteristic of the occupant based on at least one of the occupant health data and the occupant state data. In one example, vehicle system 78 is determined based on occupant health data, occupant state data, and predetermined criteria. Control system 16 recommends that occupant 13 activates vehicle system 78 to improve the wellness or comfort level of occupant 13 as suggested in FIG. 11B.

Control system 16 activates a vehicle system 78 based on at least one of the occupant health data, the occupant state data, and input from the occupant. Activated vehicle system 78 may be the same or different than the recommended vehicle system 78. For example, control system 16 recommends activating massage system 86, but activates temperature system 82 based on occupant input. In another example, control system 16 recommends activating massage system 86 and activates massage system 86 based on occupant input or occupant health data.

Control system 16 is configured to associate activation of vehicle system 78 with the occupant health data and the occupant state data in a unique occupant data profile. The unique occupant data profile is specific to one occupant and more information is added to unique occupant data profile over time to increase the accuracy and effectiveness of the recommendations made by control system 16. Control system is configured to identify occupant 13 based on at least one of input from occupant 13 and the occupant health data.

Data associated in unique occupant data profile includes occupant height, weight, sex, and age data. Such data may be entered manually by occupant 13, by smart device 40, and/or by an internet connection. Unique occupant data profile further includes a medical history including medical conditions of occupant 13. A completion level of the unique occupant data profile may be depicted by shading of silhouette from foot to head. No shading corresponds to an incomplete profile and full shading corresponds to a complete profile.

By associating associate activation of vehicle system 78 with the occupant health data and the occupant state data in the unique occupant data profile, control system 16 learns occupant preferences and behaviors over time. If the recommended vehicle system 78 is activated, control system 16 learns that occupant 13 agrees with that recommendation while occupant 13 exhibits that occupant health data and occupant state data. If the recommended vehicle system 78 is not activated and instead, another vehicle system 78 is activated, control system 16 learns that occupant 13 prefers the other vehicle system 78 while occupant 13 exhibits that occupant health data and occupant state data. Control system 16 learns and improves its recommendations as the number of iterations increase.

Control system 16 is configured to determine the effectiveness of activating vehicle system 78. Control system 16 monitors and analyzes the physiological and behavioral data of occupant 13 to determine the effect of vehicle systems 78 on occupant 13. In one example, control system 16 is configured to receive supplemental occupant-body signals and supplemental behavioral signals after activating the vehicle system. Control system 16 determines supplemental occupant health data based on the supplemental occupant-body signals and the supplemental behavioral signals. Control system 16 determines supplemental occupant state data based on the supplemental occupant health data.

Control system 16 identifies a vehicle system 78 configured to change at least one physiological characteristic or behavioral characteristic of occupant 13 based on at least one of the supplemental occupant health data, the supplemental occupant state data, and the unique occupant data profile. Control system 16 activates a vehicle system 78 based on at least one of the supplemental occupant health data, the supplemental occupant state data, the unique occupant data profile, and input from occupant 13. The activated vehicle system 78 may be the same or different than the previously activated or recommended vehicle system 78.

The control system 16 is configured to associate activation of the vehicle system 78 with the supplemental occupant health data and the supplemental occupant state data in the unique occupant data profile to learn occupant behavior and preferences. Control system 16 compares the occupant health data and the supplemental occupant health data and associates changes to the occupant health data in the unique occupant data profile.

Figure 11C:
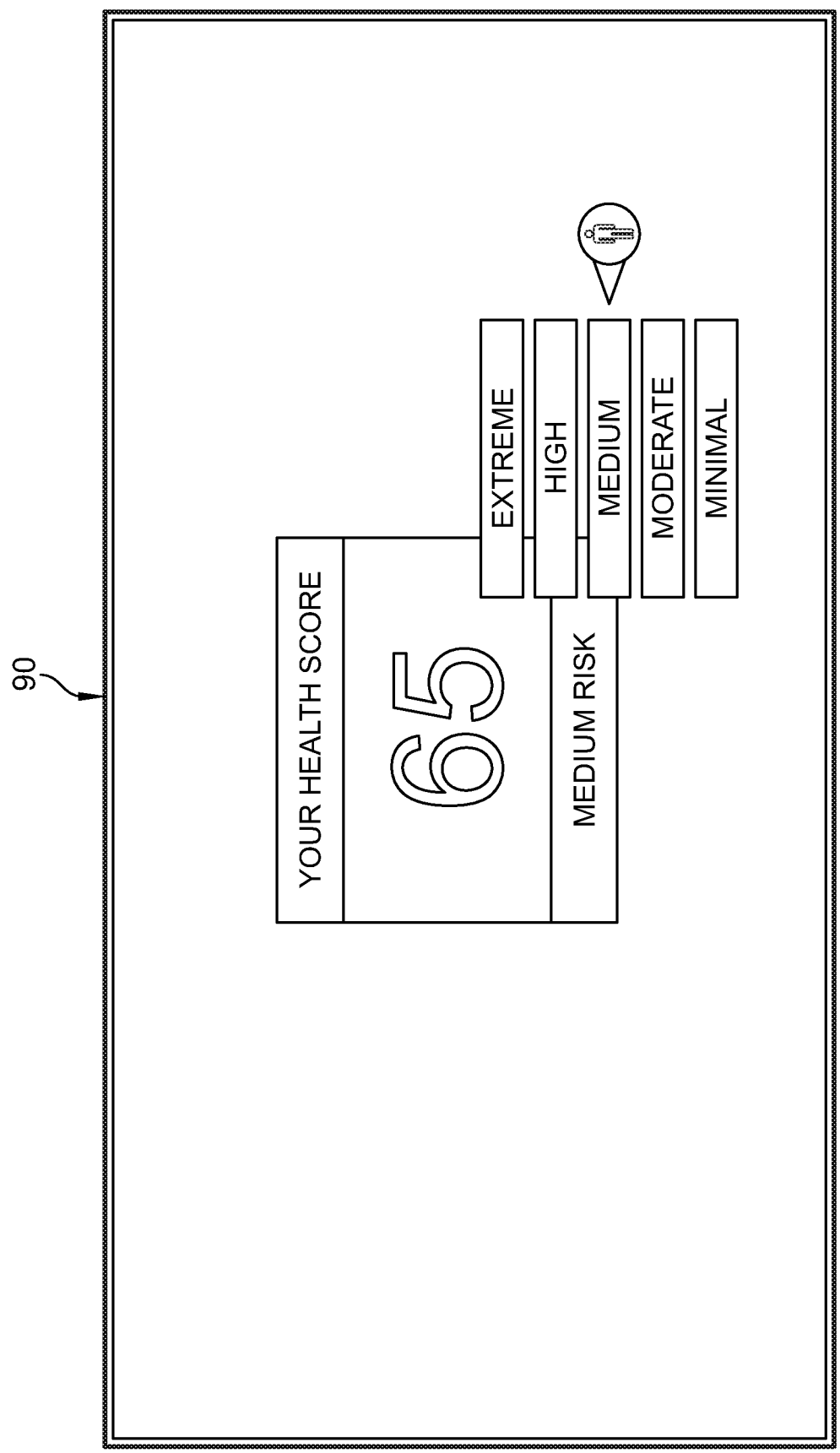
FIG. 11C is a diagrammatic view of the display included in the occupant support system showing that the occupant support system is configured to display a health score of the occupant.
Figure 12:
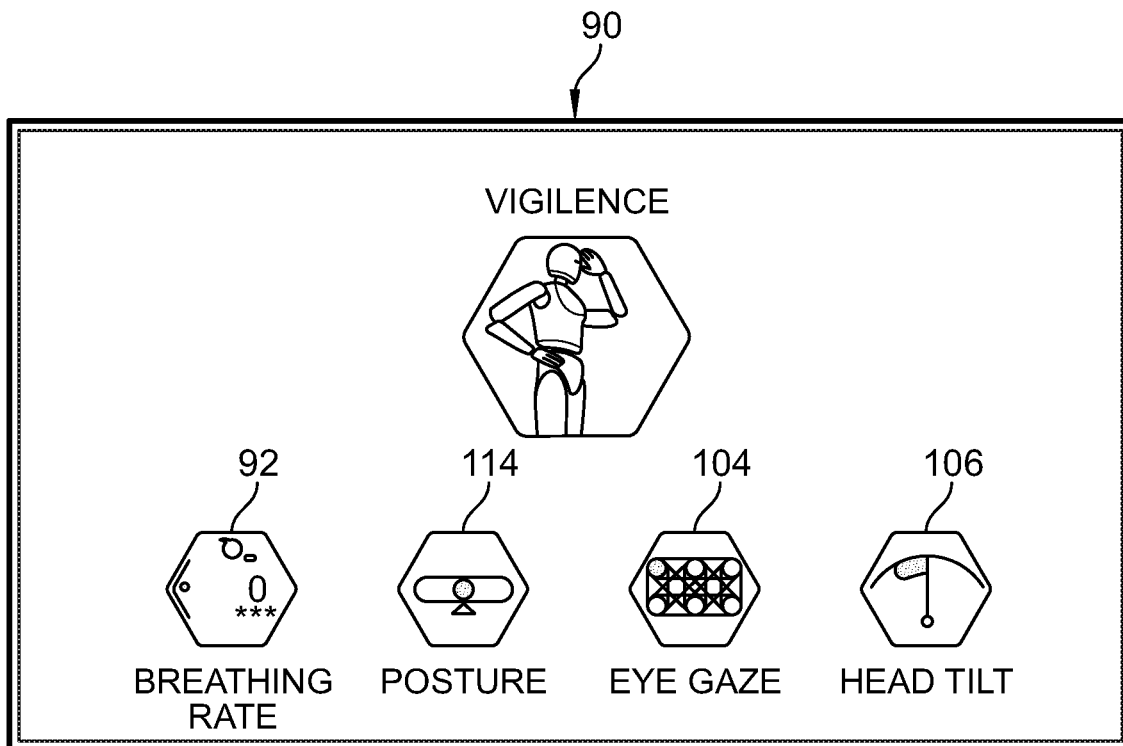
FIG. 12 is a diagrammatic view of the display included in the occupant support system showing occupant state data and, in particular, showing indicia associated with a vigilance of the occupant and suggesting that the vigilance of the occupant is based on a breathing rate of the occupant, a posture of the occupant, an eye gaze of the occupant, and a head tilt of the occupant.

Control system 16 determines a health score of occupant 13 in some embodiments, as suggested in FIG. 11C. Control system 16 is configured to receive secondary health data unique to occupant 13 from at least one of an input and an accessory device. For example, secondary health data includes a height, sex, weight, and/or age of occupant 13. Secondary health data may include a medical history and medical conditions of occupant 13 input manually or received via a smart device or over an internet connection. Control system 16 associates the secondary data with the unique occupant data profile and determine the health score of occupant 13. Control system 16 generates instructions to display the health score to occupant 13 as suggested in FIG. 11C.

In one example, the health score is based on the occupant health data, the unique occupant data profile, and predetermined criteria. In another example, the health score is based on the occupant health data, the unique occupant data profile, the secondary health data, and predetermined criteria. In some embodiments, the health score is based on cloud data of other vehicle occupants.

In some embodiments, control system 16 analyzes the occupant data over a period of time and provides a raw health score. The raw scores are tallied and compared to predetermined criteria. The raw scores are normalized for the occupant's particular occupant profile and history. The control system 16 generates instructions for outputting the health score.

Control system 16 receives schedule data indicative of scheduled events of occupant 13 from at least one of an input and an accessory device, such as, for example, smart device 40 and to prompt occupant 13 to perform an activity based on the schedule data. For example, control system 16 may remind occupant 13 of an upcoming birthday and recommend stopping for a birthday card or present. As another example, control system 16 reminds occupant 13 to take medication at a preset time.

In some embodiments, control system 16 anticipates occupant's 13 use of vehicle amenities and therapies such as, for example, vehicle systems 78. Occupant 13 is connected with occupant support system 10 via smart devices 40. Smart devices 40 provide occupant support system 10 with reminders such as reminders for meetings, birthdays, and taking medication. Control system 16 recommends external activities such as, for example, a coffee break if the occupant is about to experience drowsiness as determined based on occupant health data, occupant state data, and previous data associated in the unique occupant data profile.

In one example, the occupant state data is indicative of a vigilance of occupant 13. The vigilance of occupant 13 is based on occupant health data that includes information indicative of the respiration rate of the occupant included in signals received from piezoelectric sensor 28 and electrode 30, posture 114 of occupant 13 included in signals received from load cell(s) 34 and optical camera system 26, eye gaze 104 of the occupant included in signals received from optical camera system 26, and head tilt 106 of occupant 13 included in signals received from optical camera system 26.

In another example, vigilance is determined based on one or more of recent activities of occupant 13, audio settings of sound system 80, respiration rate 92 of occupant 13, posture 114 of occupant 13, eye gaze 104 of occupant 13, and head tilt 106 of occupant 13.

Figure 13:
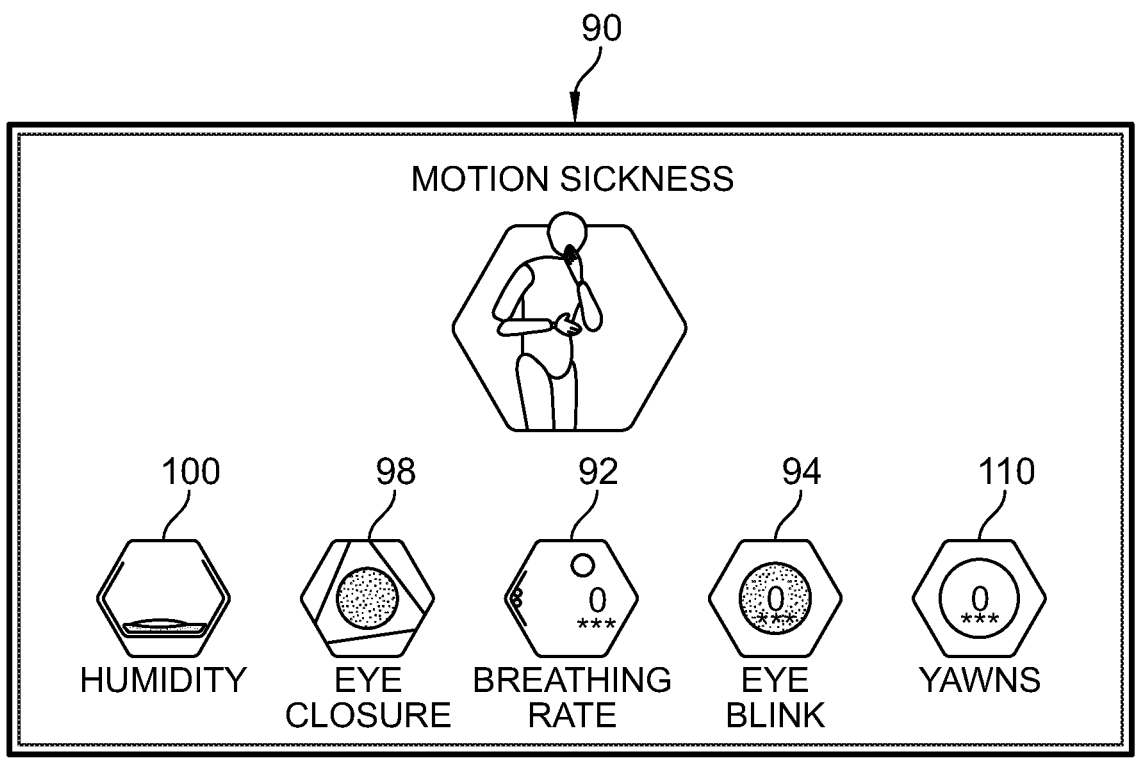
FIG. 13 is a diagrammatic view of the display included in the occupant support system showing occupant state data and, in particular, showing indicia associated with a motion sickness of the occupant and suggesting that the motion sickness of the occupant is based on humidity around the occupant, an eye closure of the occupant, a breathing rate of the occupant, an eye blink rate of the occupant, and a yawn rate of the occupant.

In another example, the occupant state data is indicative of a motion sickness of the occupant as suggested in FIG. 13. The motion sickness is based on occupant health data that includes information indicative of a humidity around occupant 13 included in signals received from humidity sensor 36, eye closure level 98 of occupant 13 included in signals received from optical camera system 26, eye blink rate 94 of occupant 13 included in signals received from optical camera system 26, yawn rate 110 of occupant 13 included in signals received from optical camera system 26, and the breathing rate 92 of occupant 13 included in signals received from piezoelectric sensor 28 and electrode 30.

In another example, motion sickness is determined based on one or more of accelerometer data, skin color change determined by signals from optical camera system 26, humidity around occupant 13, eye closure level 98 of occupant 13, breathing rate 92 of occupant 13, eye blink rate 94 of occupant 13, and yawn rate 110 of occupant 13. In yet another example, motion sickness is determined based on humidity around occupant 13, respiration rate of occupant 13, eye closure level 98 of occupant 13, and skin color change of occupant 13.

Occupant support system 10 reduces the likelihood of motion sickness, for example, in a comfortable reading scenario. Occupant support system 10 asks occupant 13 if they would like to recline to a position that is a better fit for long-term screen-viewing. Eye gaze locations and direction may be factors used in the system assessment for optimal positioning.

Figure 14:
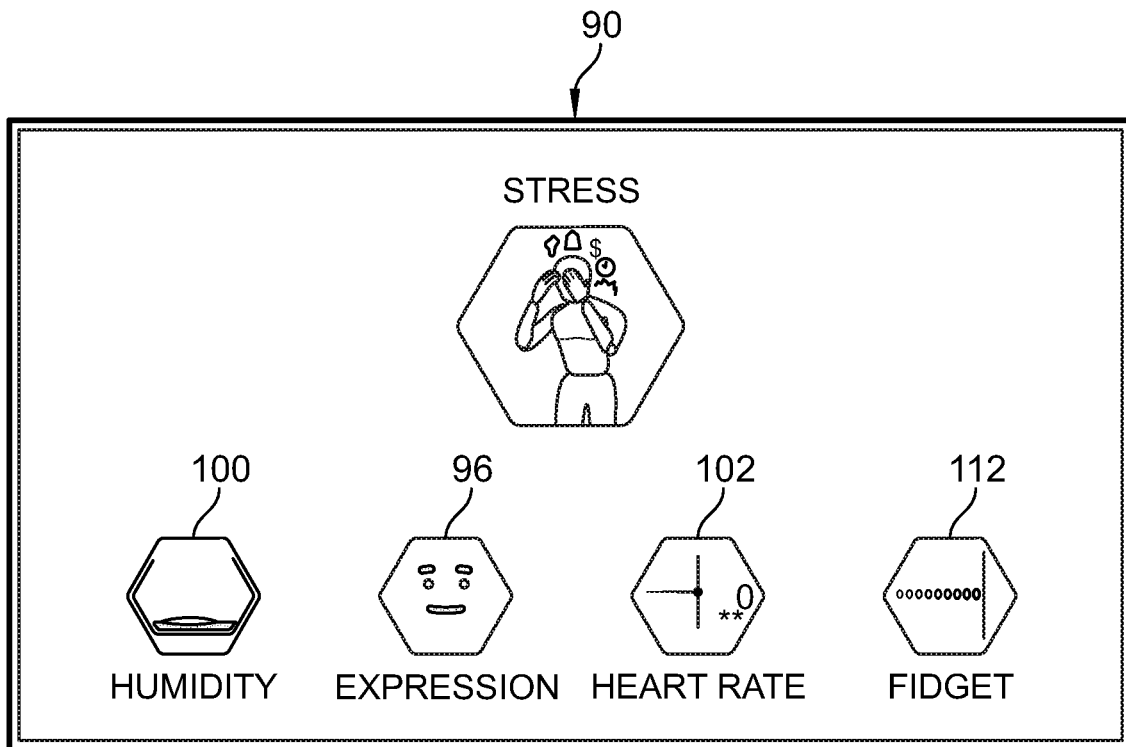
FIG. 14 is a diagrammatic view of the display included in the occupant support system showing occupant state data and, in particular, showing indicia associated with a stress of the occupant and suggesting that the stress of the occupant is based on humidity around the occupant, an expression of the occupant, a heart rate of the occupant, and a fidget level of the occupant.

In another example, occupant state data is indicative of a stress of occupant 13 as suggested in FIG. 14. The stress of occupant 13 is based on occupant health data that includes information indicative of humidity 100 around occupant 13 included in signals received from humidity sensor 36, the facial expression 96 of occupant 13 included in signals received from optical camera system 26, heart rate 102 of occupant 13 included in signals received from piezoelectric sensor 28 and electrode 30, and fidget level 112 of occupant 13 included in signals received from optical camera system 26, capacitive sensor 32, and load cell(s) 34.

In another example, stress of occupant 13 is based on one or more of the heart rate variability of occupant 13, humidity 100 around occupant 13, facial expression 96 of occupant 13, heart rate 102 of occupant 13, and fidget level 112 of occupant 13. In one example, stress of occupant 13 is based on the heart rate variability of occupant 13, humidity 100 around occupant 13, the facial expression 96 of occupant 13, and heart rate 102 of occupant 13.

Figure 15:
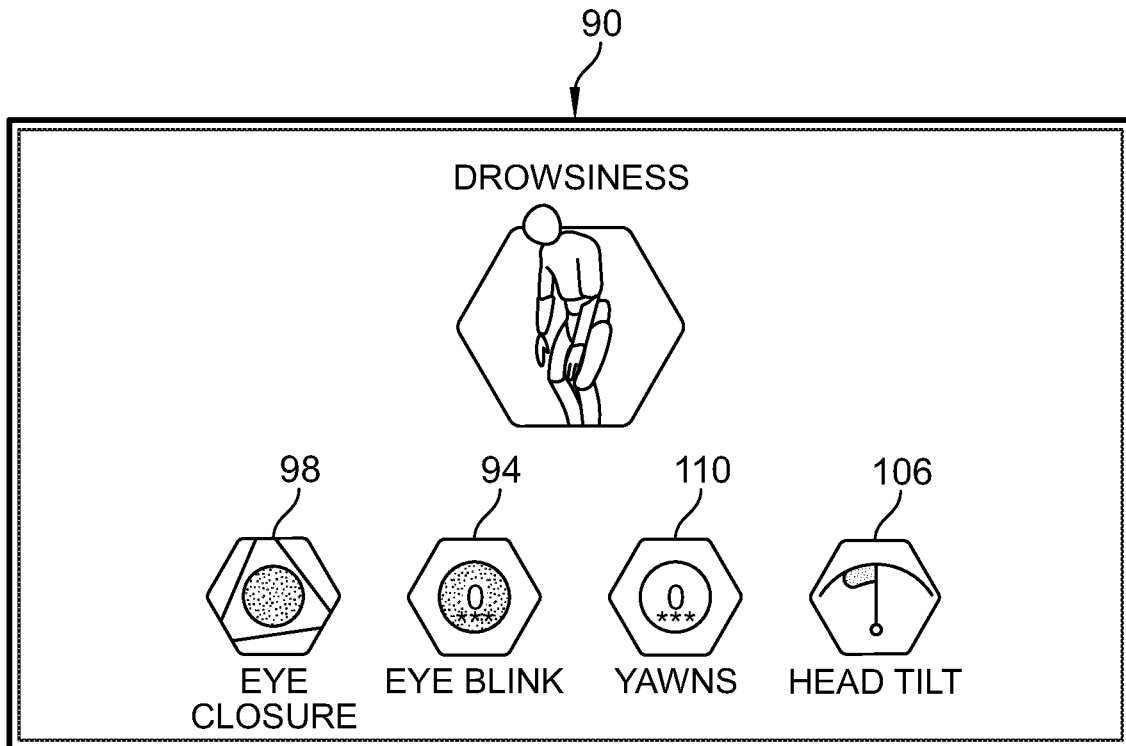
FIG. 15 is a diagrammatic view of the display included in the occupant support system showing occupant state data and, in particular, showing indicia associated with a drowsiness of the occupant and suggesting that the drowsiness of the occupant is based on an eye closure of the occupant, an eye blink rate of the occupant, a yawn rate of the occupant, and a head tilt of the occupant.

In another example, the occupant state data is indicative of a drowsiness of occupant 13 as suggested in FIG. 15. The drowsiness of occupant 13 is based on occupant health data that includes information indicative of the eye closure level 98 of occupant 13, the eye blink rate 94 of occupant 13, yawn rate 110 of occupant 13, and the head tilt 106 of occupant 13, each included in signals received from optical camera system 26.

Figure 16:
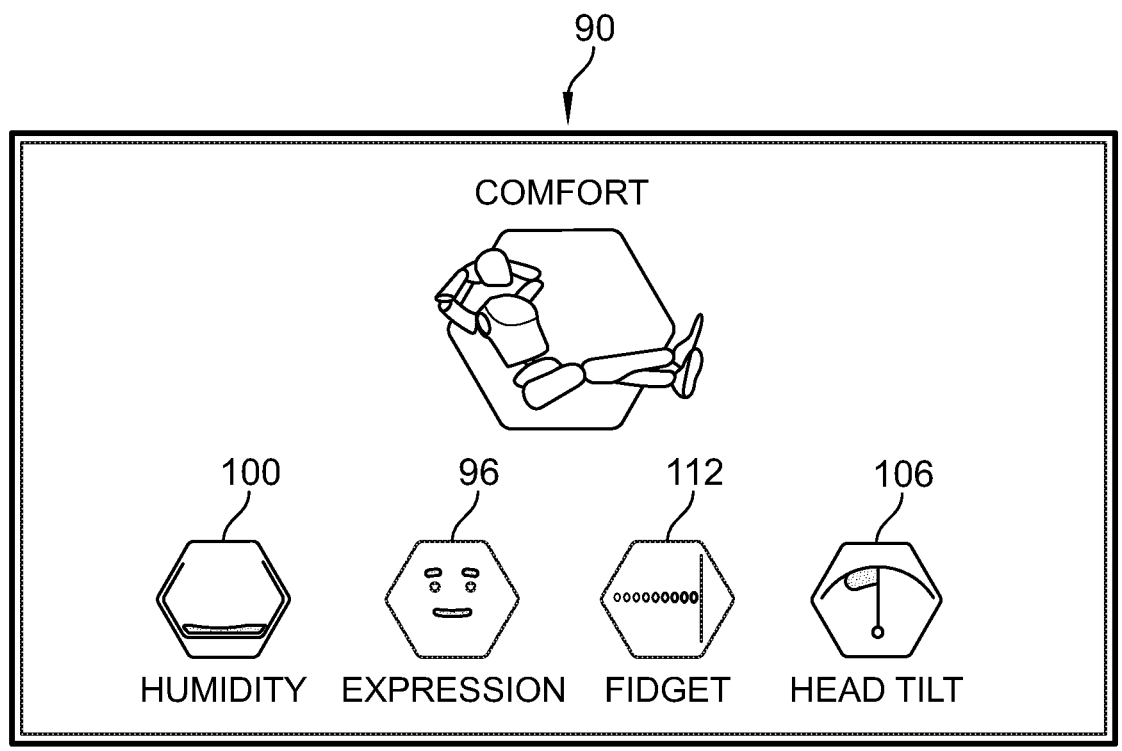
FIG. 16 is a diagrammatic view of the display included in the occupant support system showing occupant state data and, in particular, showing indicia associated with a comfort of the occupant and suggesting that the comfort of the occupant is based on humidity around the occupant, an expression of the occupant, a fidget level of the occupant, and a head tilt of the occupant.

In another embodiment, occupant state data is indicative of a comfort of occupant 13 as suggested in FIG. 16. Occupant comfort is based on occupant health data that includes information indicative of humidity 100 around occupant 13 included in signals received from humidity sensor 36, the facial expression 96 of occupant 13 included in signals received from optical camera system 26, fidget level 112 of occupant 13 included in signals received from optical camera system 26, capacitive sensor 32, and load cell(s) 34, and head tilt 106 of occupant 13 included in signals received from optical camera system 26.

In another example, occupant comfort is based on one or more of the temperature of occupant 13, a pressure distribution of occupant 13, humidity 100 around occupant 13, the expression 96 of occupant 13, fidget level 112 of occupant 13, and the head tilt 106 of occupant 13. In another example, occupant comfort is based on the temperature of occupant 13, humidity 100 around occupant 13, the expression 96 of occupant 13, and the head tilt 106 of occupant 13.

In one scenario, occupant support system 10 detects that occupant 13 has not been moving enough for optimal long-term comfort. Occupant support system 10 suggests comfort rejuvenation, which may include a rigorous massage and activation of ventilation based on sensor measurements. In another scenario, occupant support system 10 prepares occupant 13 for physical activity by giving a stretching massage. Occupant support system 10 provides certain colors and patterns of lighting to stimulate the body for upcoming activity (for example, blue light for stimulating serotonin production).

Each occupant health data type is rated as normal, high, or low in some embodiments. If one or more of the occupant health data used to determine an occupant state is not normal, control system 16 determines one or more vehicle system 78 to recommend to occupant 13 in order to change the occupant health data toward normal. Occupant health data and occupant state data is continually monitored and recommendations are provided until occupant health data and occupant state data are normal. Occupant medical history and conditions are taken into account in determining normal occupant health data and occupant state data.

Figure 17:
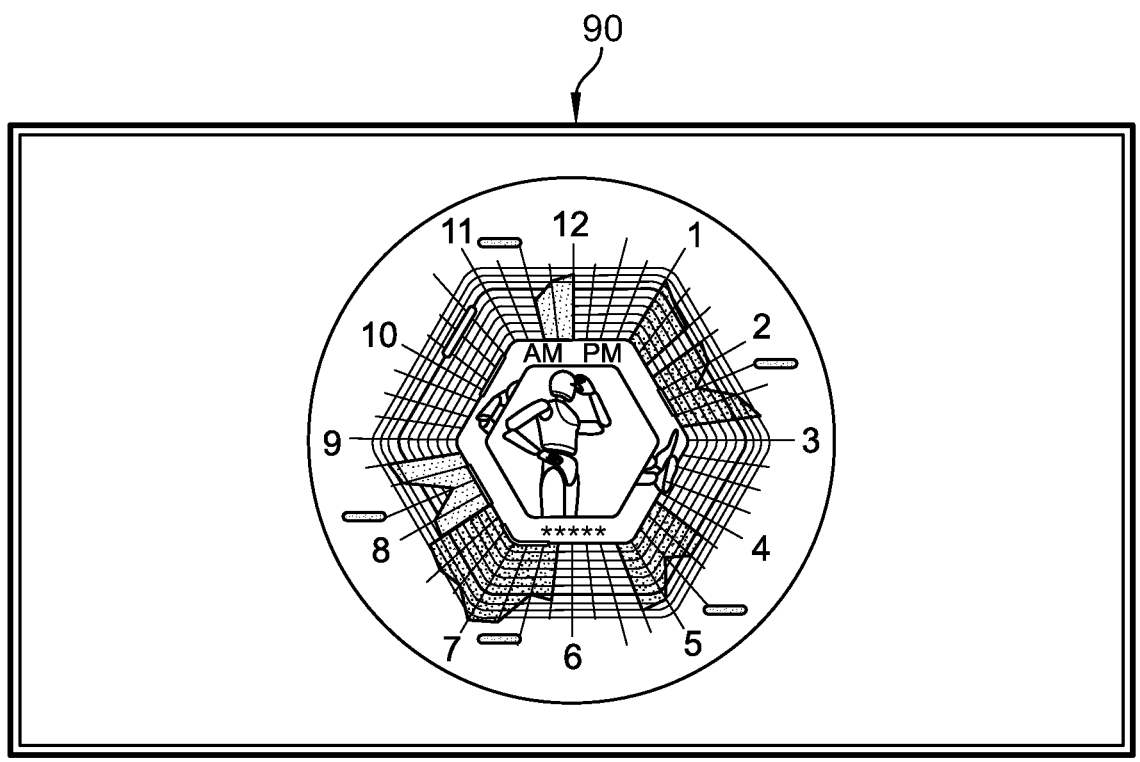
FIG. 17 is a diagrammatic view of the display included in the occupant support system showing graphical occupant health data for a 12 hour time period.

Control system 16 is configured to generate instructions to display occupant health data and/or occupant state data in a graphical representation as shown in FIG. 17. The occupant health data and/or occupant state data is graphed over a 12-hour period in the illustrative embodiment.

Occupant support system 10 is configured to cooperate with vehicle 11 and/or vehicle systems 78 to move vehicle 11 between a manual operation mode in which occupant 13 drives vehicle 11 and an autonomous operation mode in which vehicle 11 drives itself. A method 200 of moving vehicle 11 between manual operation mode and autonomous (self-driving) operation mode is shown in FIG. 18.

Method 200 includes a number of stages as suggested in FIGS. 18-22. Method 200 includes stage 202 in which occupant support system 10 indicates to the driver that autonomous driving is available. In a stage 204, autonomous driving is engaged in response to occupant input as suggested in FIG. 19. Occupant input includes clicking a button, gazing at indicia on a screen for a predetermined time, vocally responding, etc. In a stage 206, occupant support indicates that autonomous driving is engaged. As one example, display 90 shows an overhead view of vehicle 11 and its surroundings to indicate to occupant 13 that vehicle 11 is scanning and is aware of its environment during autonomous operation mode as suggested in FIG. 19. In a stage 208, occupant support system 10 monitors occupant 13 and generates wellness recommendations as discussed in detail above.

Figure 18:
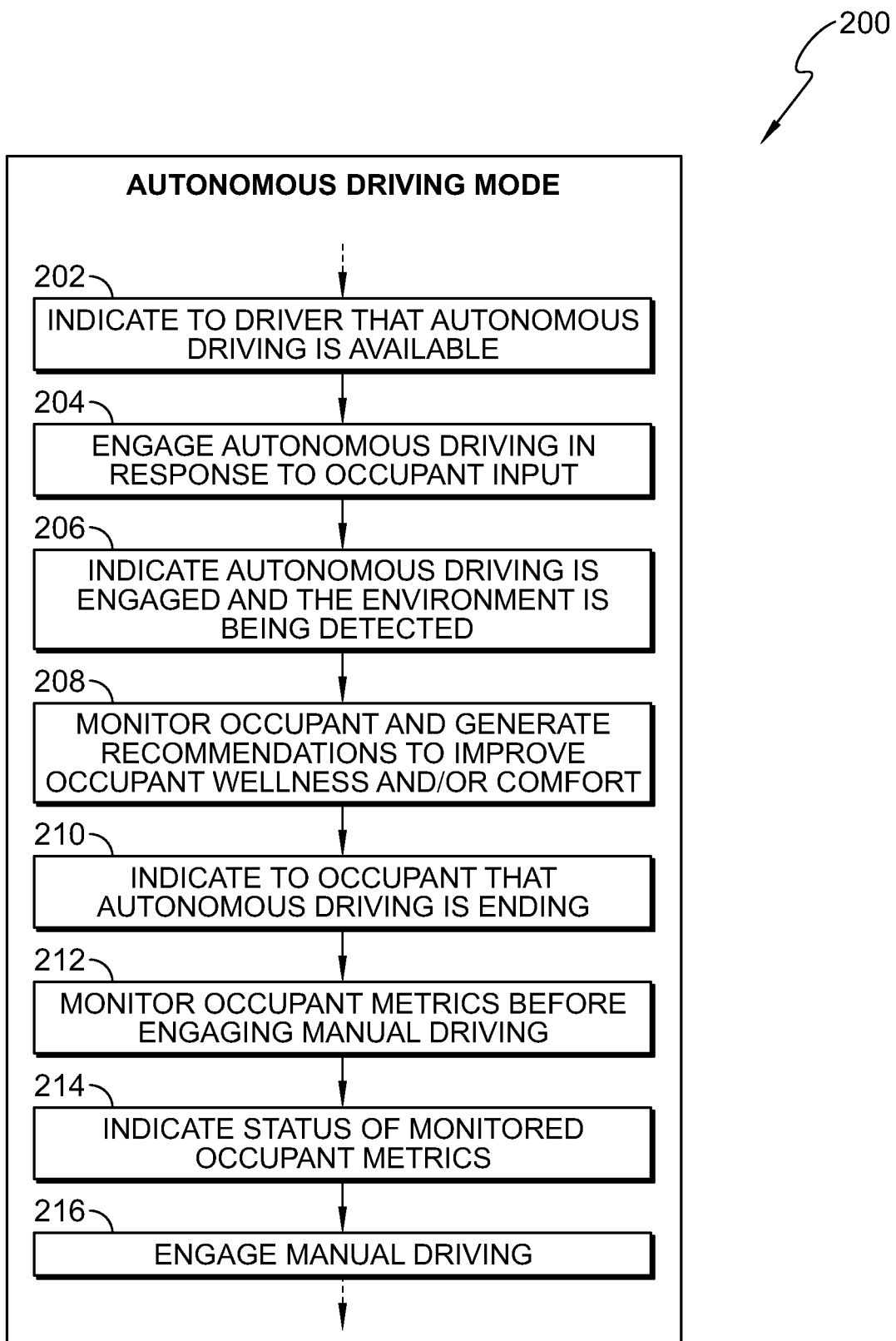
FIG. 18 is a flow chart of a method of moving the vehicle between a manual operation mode and an autonomous (self-driving) operation mode, the method including indicating to the driver that autonomous driving is available, engaging autonomous driving in response to occupant input, indicating that autonomous driving is engaged, monitoring the occupant and generating wellness recommendations, indicating that autonomous driving is ending, monitoring occupant metrics, indicating status of the occupant's metrics, and engaging manual driving.

In a stage 210, occupant support system 10 indicates that autonomous operation mode is ending as suggested in FIG. 18. In a stage 212, occupant support system 10 monitors occupant 13 metrics before moving from autonomous operation mode to manual operation mode. The status of the occupant's metrics is communicated to occupant 13 in a stage 214. Vehicle 11 engages manual operation mode in a stage 216 if occupant's metrics meet predetermined criteria as suggested in FIG. 18.

Figure 19:
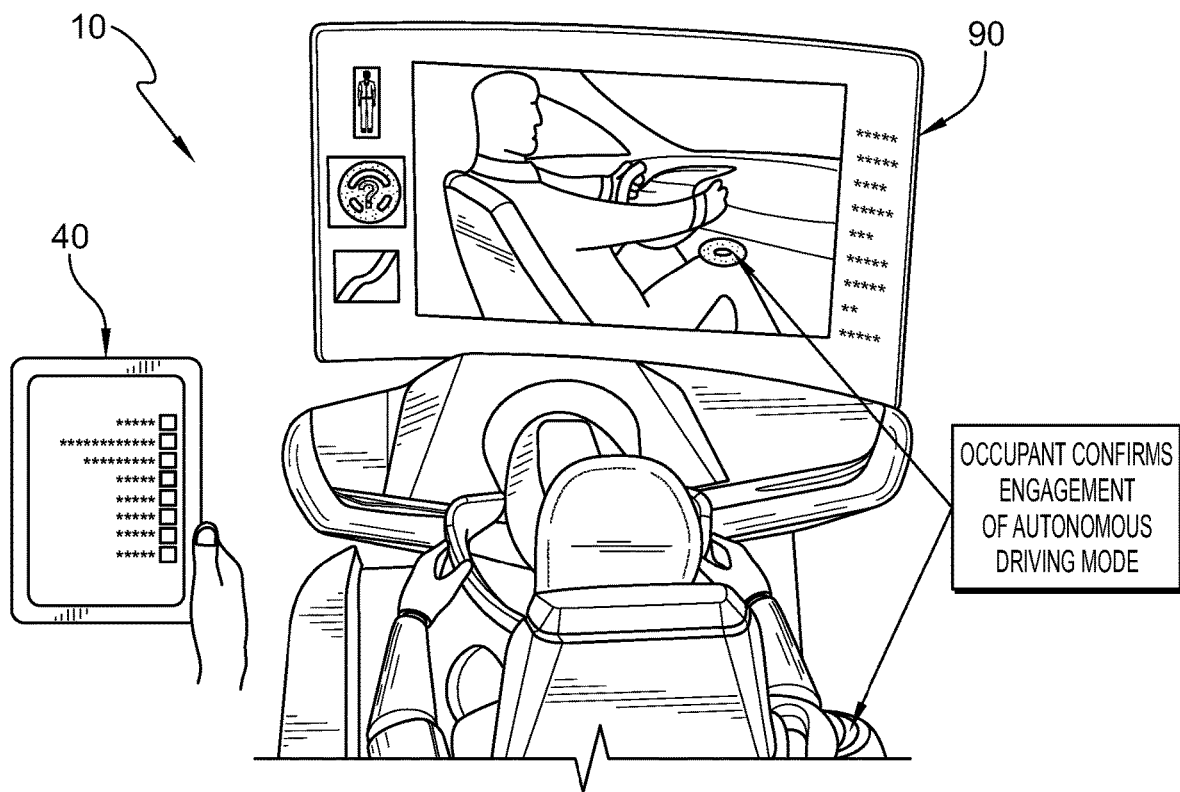
FIG. 19 is a perspective and diagrammatic view of an occupant supported in the occupant support system of FIG. 1 suggesting that the vehicle is engaging autonomous operation mode in response to the occupant's input.
Figure 20:
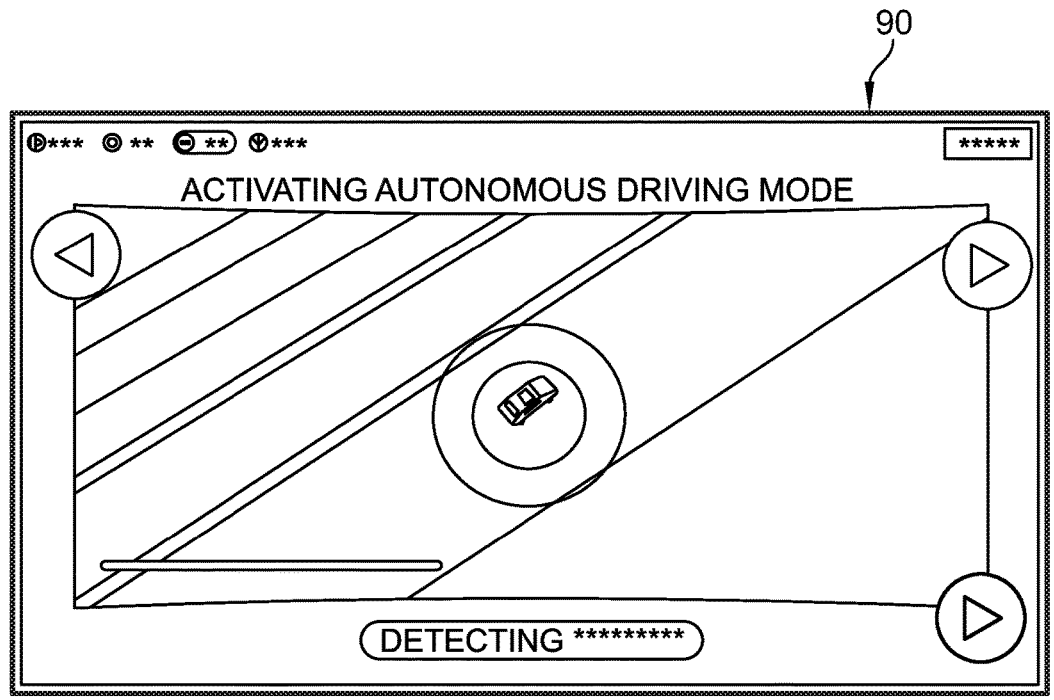
FIG. 20 is a diagrammatic view of the display included in the occupant support system showing an overhead view of the vehicle and its surroundings to indicate to the occupant that the vehicle is scanning and aware of its environment during autonomous operation of the vehicle.

Occupant 13 begins to switch from manual control of vehicle 11 to autonomous operation mode as suggested in FIG. 19. Occupant 13 affirms actions with a press of a button in the illustrative embodiment. The button may be replaced with an audible confirmation or otherwise in other embodiments. Display 90 provides a message to indicate that the occupant should "prepare to enter autonomous driving mode" and a camera angle pans backward to show the back of the occupant's head. This allows the occupant support system 10 and methods to pick out specific vehicles in the occupant vehicle's vicinity and may also indicate mirror views, giving occupant 13 confidence that the systems are aware of vehicle situational and environmental information. A specified color of light (i.e. green) on the steering column or other location indicates that occupant 13 is now clear to release the steering wheel to shift vehicle 11 into autonomous operation (self-driving) mode In stage 208, occupant 13 may perform some other activity unrelated to controlling vehicle 11. Relevant sensor data, in combination with software using proprietary algorithms, may conclude that one or more occupants are engaging in certain activities, such as reading or having a conversation with one another. Occupant support system 10 and methods provides recommendations based on the action of one or more occupants. One recommendation that the occupant may be presented with is whether or not they would like to adjust their position. As another example, if the systems conclude the occupants are engaging in light conversation, the music volume may be reduced and the lighting will be adjusted accordingly. If the systems conclude that the occupants are reading, directional light may be provided to each of the occupants and the music may be turned off.

Moreover, sensor data streams may display various indicators of what the occupant wellness systems and methods are detecting, including but not limited to, reading, conversing, adjusting position, interacting with electronic devices or other occupants, and sleeping. Occupant support system 10 and methods may provide one or more suggestions to combat the onset of motion sickness to the one or more occupants of the vehicle. The occupant(s) may affirm any request for action from the system with a press of a button. In illustrative embodiments, user activities to be learned and tracked by the systems and methods include, but are not limited to, reading, sleeping, writing, talking, looking out a window, manually-controlled driving, and autonomous-mode driving.

Figure 21:
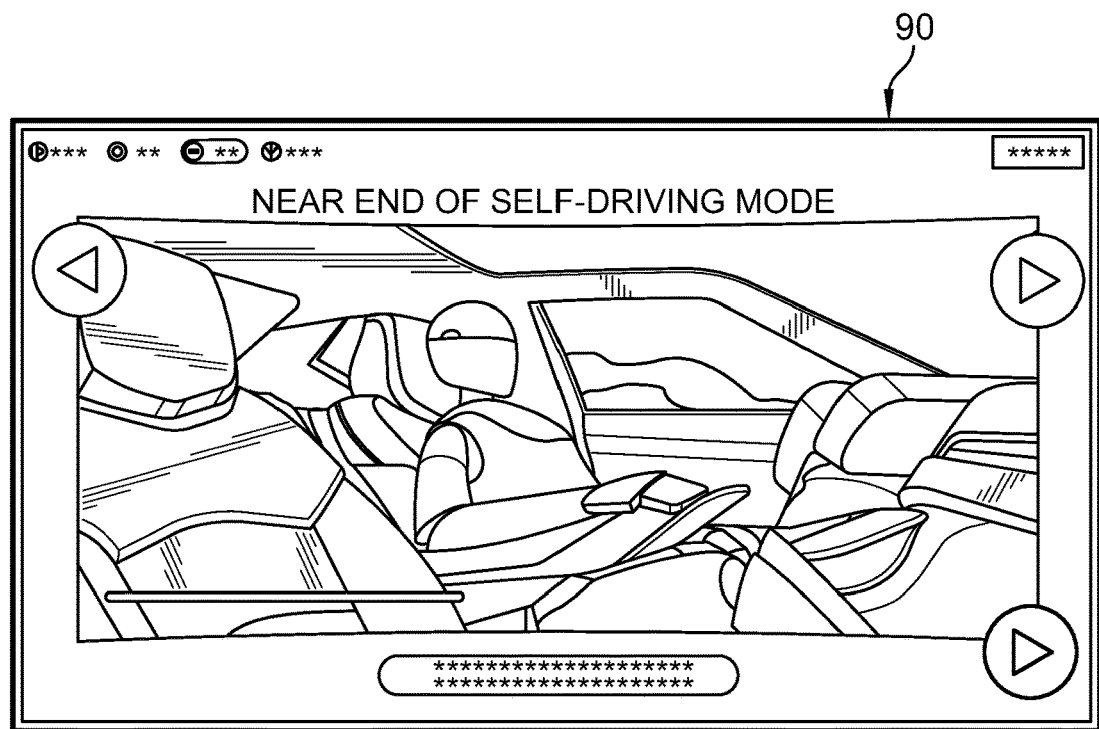
FIG. 21 is a diagrammatic view of the display included in the occupant support system showing that autonomous operation mode is ending and suggesting that the posture and position of the occupant is being monitored before the vehicles moves into the manual operation mode.
Figure 22:
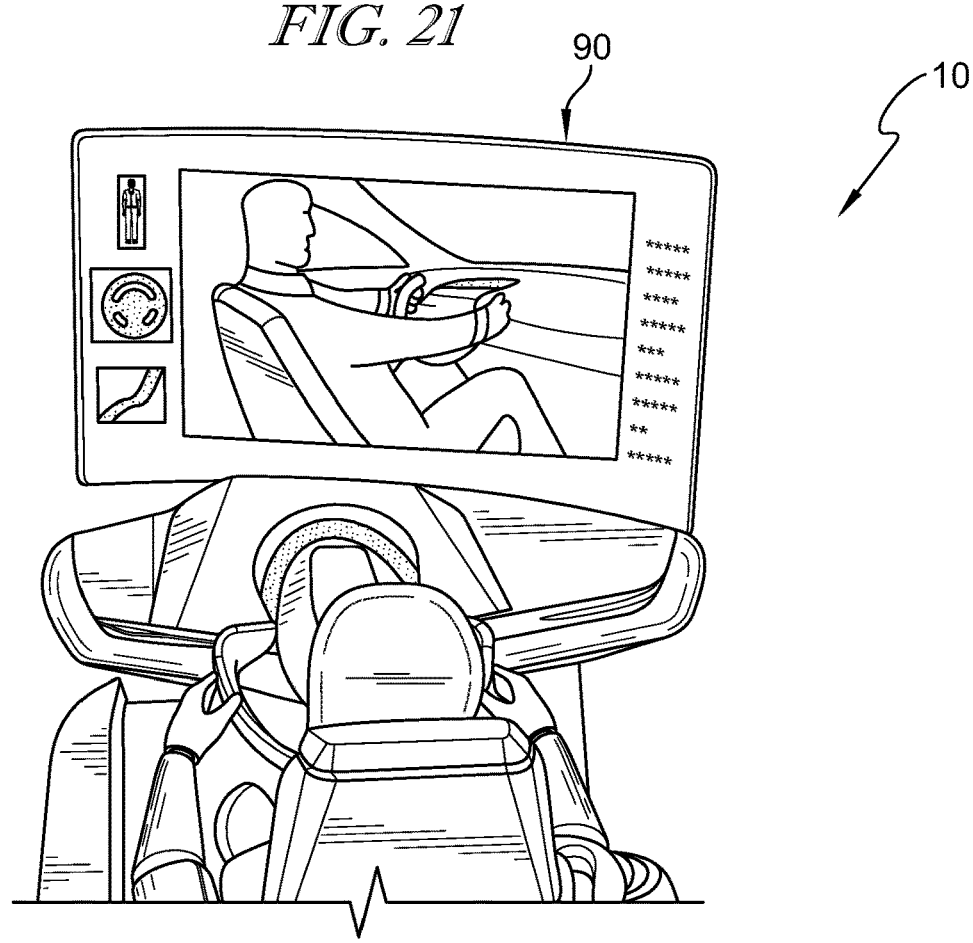
FIG. 22 is a perspective view of the occupant support system of FIG. 19 showing that the display suggests that the occupant should place their hands on the steering wheel and that hand position of the occupant is being monitored before the vehicle moves into the manual operation mode.
Figure 23:
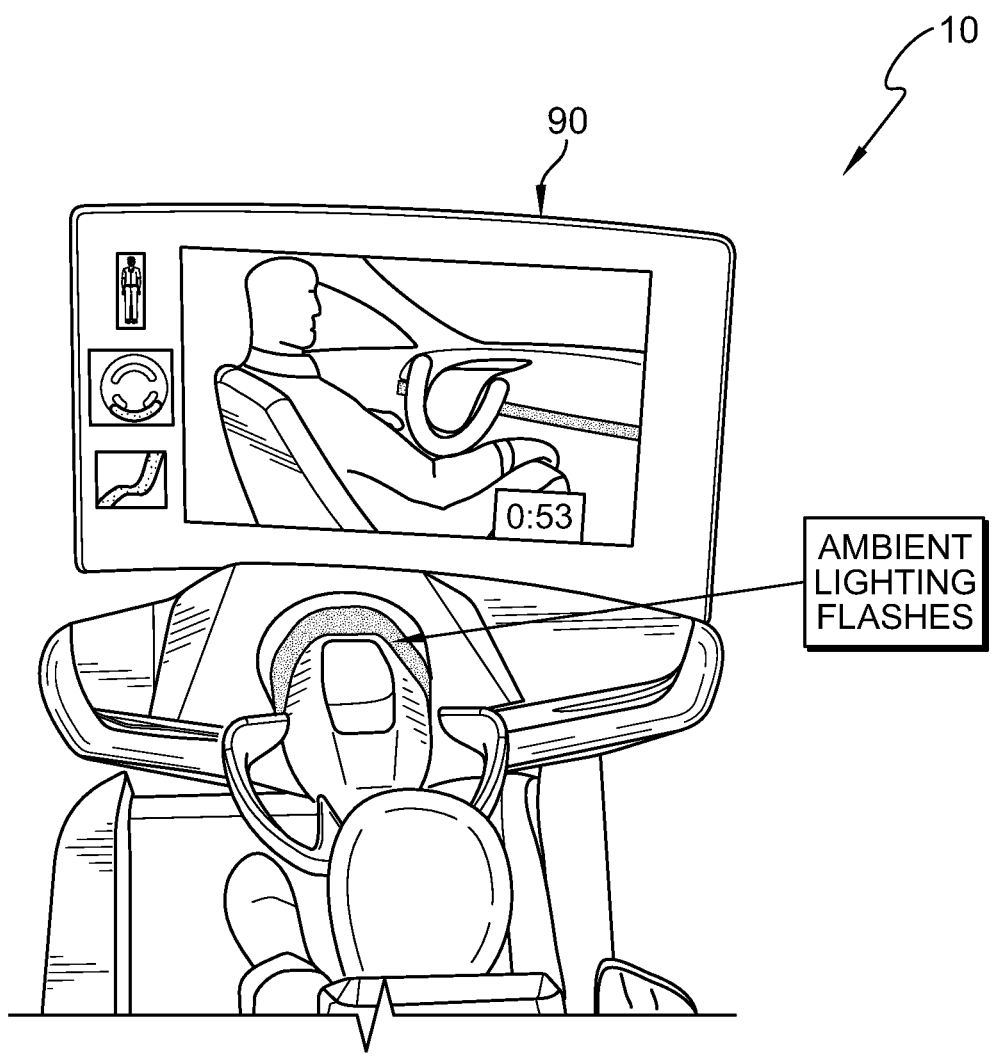
FIG. 23 is a view similar to FIG. 22 showing that the gaze of the occupant is being monitored before the vehicle moves into the manual operation mode.

During stage 212, occupant support system 10 monitors occupant body position, occupant hand position, and occupant gaze as suggested in FIGS. 21-23. If occupant body position is in a predetermined arrangement, occupant support system 10 determines that occupant body position is ready for manual operation as suggested in FIG. 21. As a result, an indication such as, for example, a light on the steering column may change (i.e. from red to green). If occupant body position is not in a predetermined arrangement, occupant support system 10 recommends changing the arrangement of seat 12 or automatically changes the arrangement of seat 12 to a predetermined arrangement.

Occupant hand position is monitored by occupant support system 10 as suggested in FIG. 22. If occupant hand position is in a predetermined arrangement, occupant support system 10 determines that occupant hand position is ready for manual operation. As a result, an indication such as, for example, a light on the steering column may change (i.e. from red to green). If occupant hand position is not in a predetermined arrangement, occupant support system 10 recommends changing the arrangement of occupant's hands.

Eye glance direction and other factors (eye tracking, face tracking, or both) shows occupant 13 is focusing in on a different field of view as suggested in FIG. 23. Mirrors may flash on-screen to evaluate the occupant's 13 awareness based upon time to focus. One or more timers may indicate elapsed time since the reengagement sequence began. Occupant looks forward at a horizon for two seconds (or other predetermined amount of time), and as a result, the ambient lighting display or a steering column light turns green to indicate that occupant 13 is ready to assume manual driving. In some embodiments, vehicle 11 audibly announces that occupant 13 is ready to drive.

The present disclosure relates, at least in part, to fatigue detection and prediction of occupant 13 of occupant support system 10. The fatigue detection and prediction may be based on a number of factors. An occupant-driver fatigue curve may be projected to occupant 13 and may help schedule a trip to minimize fatigue before the trip starts. The system may inform or suggest to the driver when and where to take a break from driving, as well as provide reminders for a break during the trip. Occupant may 13 provide inputs and at least portions of the operator profile to the system. Preference modifications may be provided by the system and considered in planning for restorative sleep in a multi-day journey.

Figure 24:
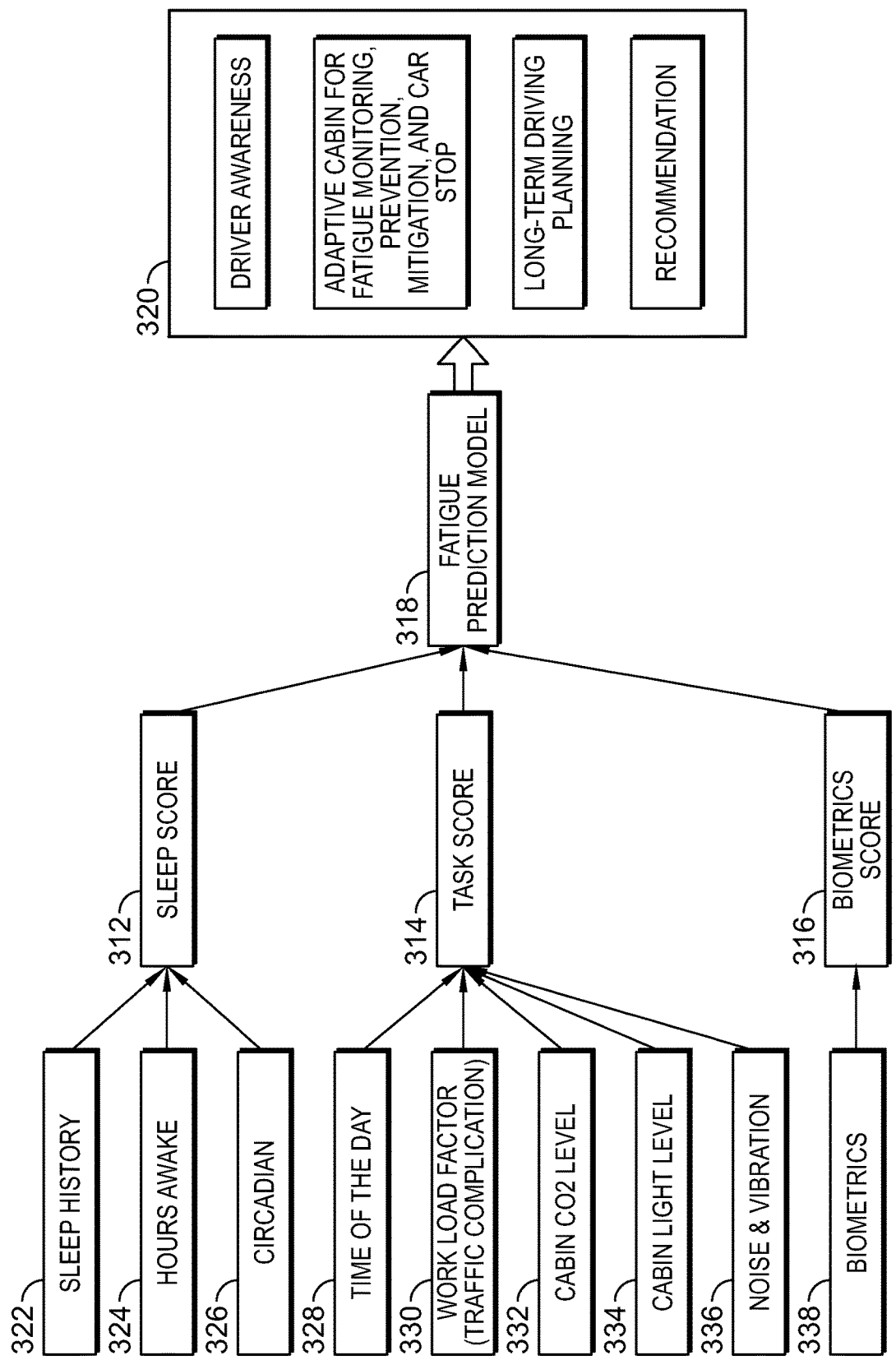
FIG. 24 is a diagrammatic view of the occupant support system of FIG. 1 showing that the occupant support system is adapted to generate a sleep score, a task, score, and a biometrics score from the plurality of input received from the sensor system, determine a fatigue of the occupant, and to generate actions and recommendations based on the sleep score, task score, and biometrics score.
Figure 25:
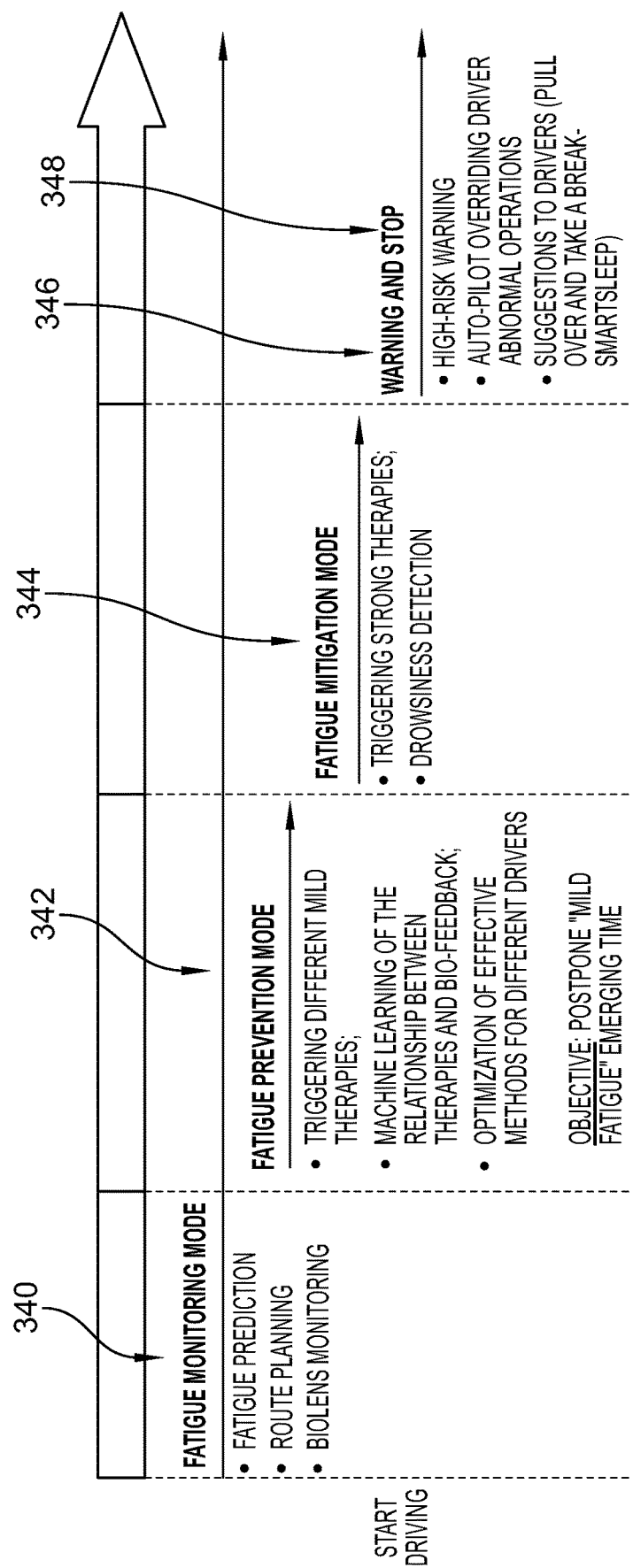
FIG. 25 is a diagrammatic view showing that the occupant support system of FIG. 1 is operable in a fatigue monitoring mode, a fatigue prevention mode, a fatigue mitigation mode, a warning mode, and a stop mode.

Occupant support system 10 is configured to monitor occupant fatigue using biometric and sleep characteristics of occupant 13 as well as vehicle/environmental characteristics as suggested in FIGS. 24-26. Occupant support system 10 may further include the unique occupant data profile while monitoring and addressing occupant fatigue. Occupant support system 10 is configured to determine a sleep score 312, a task score 314, and biometrics score 316 based on the monitored characteristics and to determine a fatigue of occupant 13 based on the sleep score 312, task score 314, and biometrics score 316.

Occupant support system 10 activates vehicle systems 78 or generates recommendations to minimize occupant fatigue based on the occupant fatigue. For example, occupant support system 10 may recommend activating a massage system 86 to improve occupant's comfort and blood flow or recommend a coffee break if occupant 13 is likely to be fatigued. Over time, occupant support system 10 obtains more and more data and occupant feedback to improve its recommendations and, thereby, minimize occupant fatigue.

Occupant support system 10 includes seat 12, sensor system 14, and control system 16 as shown in FIGS. 1 and 2. Seat 12 includes seat bottom 18 coupled to the floor of vehicle 11 and seat back 20 that extends upwardly away from seat bottom 18. Sensor system 14 includes the plurality of sensors configured to measure and obtain occupant physiology, occupant behavior, occupant sleep information, surrounding environment information, and vehicle information as suggested in FIGS. 3-8 and 24. Control system 16 analyzes the information from sensor system 14 and determines occupant fatigue. Control system 16 generates recommendations and activates vehicle systems 78 for minimizing occupant fatigue.

Control system 16 determines sleep score 312, task score 314, and biometrics score 316 indicative of sleep characteristics, vehicle and environmental characterizes, and physiological and behavioral characteristics of occupant 13 based on the signals from sensor system 14 as suggested in FIG. 24. Control system 16 analyzes sleep score 312, task score 314, and biometrics score 316 and determines occupant fatigue. Control system 16 generates recommendations for minimizing occupant fatigue.

Vehicle system 78 may be activated automatically by control system 16 or manually by occupant 13 in response to a recommendation. Alternatively, occupant 13 may activate a different vehicle system 78. Control system 16 monitors which vehicle system(s) 78 is activated and the effect on the occupant fatigue. Control system 16 associates the selected vehicle system 78, the occupant fatigue, and sleep score 312, task score 314, and biometrics score 316 in a unique occupant data profile to learn occupant preferences and effective recommendations.

Future recommendations may be based on the occupant's preferences and effective recommendations such that they are more tailored to occupant 13 over time. Recommendations may also include external activities and therapies. For example, control system 16 may determine that occupant 13 is or will likely be fatigued and recommend taking a break from driving.

Advanced analytics may be used for identifying correlations between occupant 13 and the events experienced to suggest action using recommendations. Suggested actions result from advanced analytics of similar occupant profiles on the cloud with similar situational data, for example a pool of participant data that has already experienced the situation this particular occupant is experiencing, to make recommendations to this particular occupant 13 in some embodiments.

Sensor system 14 includes the plurality of sensors as shown in FIGS. 3-10 and discussed above. Measurements from sensor system 14 are used to determine sleep score 312, task score 314, and biometrics score 316 as suggested in FIG. 24. Sensor system 14 is configured to obtain biometrics input associated with physiological and behavioral characteristics of occupant 13 of occupant support system 10, sleep input associated with sleep characteristics of occupant 13, and vehicle input associated with characteristics of the vehicle and environment surrounding the vehicle.

Sleep inputs include one or more of sleep history 322 of occupant 13, a number of hours 324 occupant 13 has been awake or without sleep, and circadian information 326 of occupant 13 as shown in FIG. 24. Vehicle input includes one or more of a time of the day 328, a work load factor 330 such as traffic complication, a cabin carbon dioxide level 332, a vehicle cabin light level 334, and noise and vibration levels 336 as shown in FIG. 24. Biometrics inputs 338 include one or more of the data included in experience levels 1-3 shown in FIG. 3.

Control system 16 is configured to receive supplemental biometrics input after activating vehicle system 78. Control system 16 determines a supplemental biometrics score based on the supplemental biometrics input and determines occupant fatigue based on the supplemental biometrics score, the sleep score, and the task score. As such, control system 16 may monitor the effectiveness of different vehicle systems 78 as applied to occupant 13 to minimize occupant fatigue. Control system 16 is further configured to compare the biometrics score and the supplemental biometrics score and associate changes to the biometrics score in the unique occupant data profile.

Occupant support system 10 is configured to operate in one of a plurality of modes 340, 342, 344, 346, 348 to monitor and react to occupant fatigue as suggested in FIG. 25. Occupant support system 10 is operable in a fatigue monitoring mode 340, a fatigue prevention mode 342, a fatigue mitigation mode 344, a warning mode 346, and a stop mode 348.

In fatigue monitoring mode 340, occupant support system 10 provides fatigue prediction, route planning, and occupant monitoring using biolense camera system 26. In fatigue prevention mode 342, occupant support system 10 activates therapies included, for example, in vehicle systems 68, provides machine learning of relationship between therapies and bio-feedback from occupant 13, and optimizes the effect for different drivers in an effort to minimize or postpone occupant fatigue. In fatigue mitigation mode 344, occupant support system 10 activates additional therapies or increases the magnitude of therapies and provides drowsiness detection.

In warning mode 346, occupant support system 10 generates a warning signal for notifying occupant 13 of their fatigue and suggesting a break or preventative action. In stop mode 348, occupant support system 10 changes the vehicle from a manual operation to autonomous operation. In some embodiments, occupant support system 10 conducts a controlled stop of the vehicle in stop mode 348.

In another embodiment, occupant support system 10 includes fatigue mitigation mode 344, warning mode 346, and stop mode 348. Each mode may be adjusted for vehicles of varying autonomy. In some vehicles, stop mode 348 stops the vehicle in a controlled manner while, in another vehicle, stop mode 348 diverts the vehicle to a route in which the vehicle drives itself. In some embodiments, occupant support system 10 detects occupant 13 is a new driver and one or more of the modes suggests or autonomously stops the vehicle and makes a telephone call to the occupant's guardian.

Control system 16 receives inputs 322, 324, 326, 328, 330, 332, 334, 336, 338 from sensor system 14 and determines sleep score 312, task score 314, and biometrics score 316 as shown in FIG. 24. One of the plurality of operating modes 340, 342, 344, 346, 348 of occupant support system 10 is selected by control system 16 based on scores 312, 314, 316 via fatigue prediction model 318. Occupant support system 10 then operates in the selected operating mode 340, 342, 344, 346, 348. Fatigue prediction model 318 may provide a plurality of features 320 such as indicating driver awareness, adapting the cabin for the different modes 340, 342, 344, 346, 348, generating a long-term planning strategy, and generating a fatigue minimizing recommendation.

In the illustrative example, each of sleep score 312, task score 314, and biometrics score 316 have three levels as suggested in FIG. 26. The three levels include green as the lowest, yellow as intermediate, and red as the highest. In other embodiments, the levels may have different identifiers such as levels one, two, and three.

The charts 350, 360, 370 shown in FIG. 26 provide examples of selecting modes 340, 342, 344, 346, 348 based on weighing of scores 312, 314, 316. Chart 350 shows a mode selection determination based on sleep score 312 being green. Chart 360 shows a mode selection determination based on sleep score 312 being yellow. Chart 370 shows a mode selection determination based on sleep score 312 being red.

In the illustrative example, control system 16 selects fatigue monitoring mode 340 when sleep score 312 is green, biometrics score 316 is green, and task score 314 is green or yellow as shown in chart 350 of FIG. 26. Fatigue prevention mode 342 is selected when sleep score 312 is green, biometrics score 316 is yellow, and task score 314 is green or yellow and when sleep score 312 is green, biometrics score 316 is green, and task score 314 is red. Fatigue mitigation mode 344 is selected when sleep score 312 is green, biometrics score 316 is yellow, and task score 314 is red. Warning mode 346 is selected when sleep score 312 is green, biometrics score 316 is red, and task score 314 is green or yellow. Stop mode 348 is selected when sleep score 312 is green, biometrics score 316 is red, and task score 314 is red.

In the illustrative example, control system 16 selects fatigue monitoring mode 340 when sleep score 312 is yellow, biometrics score 316 is green, and task score 314 is green as shown in chart 360 of FIG. 26. Fatigue prevention mode 342 is selected when sleep score 312 is yellow, biometrics score 316 is green, and task score 314 is yellow or red and when sleep score 312 is yellow, biometrics score 316 is yellow, and task score 314 is green. Fatigue mitigation mode 344 is selected when sleep score 312 is yellow, biometrics score 316 is yellow, and task score 314 is yellow. Warning mode 346 is selected when sleep score 312 is yellow, biometrics score 316 is red, and task score 314 is green and when sleep score 312 is yellow, biometrics score 316 is yellow, and task score 314 is red. Stop mode 348 is selected when sleep score 312 is yellow, biometrics score 316 is red, and task score 314 is yellow or red.

In the illustrative example, control system 16 selects fatigue monitoring mode 340 when sleep score 312 is red, biometrics score 316 is green, and task score 314 is green as shown in chart 370 of FIG. 26. Fatigue prevention mode 342 is selected when sleep score 312 is red, biometrics score 316 is green, and task score 314 is yellow or red. Fatigue mitigation mode 344 is selected when sleep score 312 is red, biometrics score 316 is yellow, and task score 314 is green. Warning mode 346 is selected when sleep score 312 is red, biometrics score 316 is yellow, and task score 314 is yellow or red. Stop mode 348 is selected when sleep score 312 is red, biometrics score 316 is red, and task score 314 is green, yellow, or red.

In one example, biometrics input 338 includes information indicative of a respiration rate of the occupant from signals received from a piezoelectric sensor 28 and an electrode 30 included in sensor system 14. Biometrics input 338 further includes information indicative of posture of occupant 13 from signals received from load cell 34 and optical camera 26 included in sensor system 14. Biometrics input 338 further includes information indicative of the eye gaze of occupant 13 from signals received from optical camera 26. Biometrics input 338 further includes information indicative of the head tilt of occupant 13 from signals received from optical camera 26.

In another example, biometrics input 338 includes information indicative of a humidity around occupant 13 included in signals received from humidity sensor 36 included in the sensor system 14. Biometrics input 338 further includes information indicative of eye closure of occupant 13 included in signals received from optical camera 26 included in sensor system 14. Biometrics input 338 further includes information indicative of eye blink rate of occupant 13 included in signals received from optical camera 26. Biometrics input 338 further includes information indicative of the yawn rate of occupant 13 included in signals received from optical camera 26. Biometrics input 338 further includes information indicative of the breathing rate of occupant 13 included in signals received from piezoelectric sensor 28 and electrode 30 included in sensor system 14.

In yet another example, biometrics input 338 includes information indicative of an eye closure level of occupant 13. Biometrics input 338 further includes information indicative of the eye blink rate of occupant 13. Biometrics input 338 further includes information indicative of the yawn rate of occupant 13. Biometrics input 338 further includes information indicative of the head tilt of occupant 13. The eye closure level, blink rate, yawn rate, and head tilt information is included in signals received from optical camera 26 included in sensor system 14.

Occupant fatigue may be predicted, at least in part, with bio-mathematical models such as SAFTE, FAST, and FAID. These models may have limitations and may not form the only level fatigue risk management. Some may be useful to predict and minimize fatigue in particular applications. One illustrative model considers a variety of interactive factors when predicting individual current fatigue risk and performance-effectiveness level as suggested in FIG. 24. The model may consider sleep history 322, circadian factors 326, and sleep inertia 324. These factors may interact in a number of complex ways to create a model that is able to make predictions.

Knowing the real-time fatigue level of an occupant, then intervening and managing that fatigue in advance may be more effective than trying to fix issues after the onset of fatigue and drowsiness. Knowing driver fatigue levels based on real-world situations may inform the occupant (driver) when they are at risk of fatigue impairment.

The fatigue-prediction system 318 may help occupant 13 schedule times and locations to take a break, plan for the best location and time of restorative sleep, and make suggestions to take actions early toward a more energizing cabin environment. Based on the occupant-driver fatigue level, the system 10 may provide the car-to-driver hand-over assessment for a semi-autonomous scenario. For example, driver-to-car hand-over may be suggested if there is high risk of falling asleep, and a break will be recommended. The autonomous mode may engage for emergency-accident avoidance.

The fatigue prediction system 10 may include fatigue prediction input, fatigue prediction algorithms, fatigue management, and fatigue profile machine learning for intelligent improvement. The inputs include, but are not limited to, sleep-related parameters such as, for example, sleep history 322, sleep inertia 324, and circadian factors 326.

Extra-vehicle factors outside the vehicle cabin may be used as input. These factors may include, but are not limited to, traffic conditions, road dullness, and prior activities of the occupant. Inter-cabin parameters within the cabin of the vehicle may be used as input and may include, but are not limited to, the occupant profile, driver biometric history and current state, cabin light color and intensity, cabin $CO_2$ level, cabin thermal environment, and occupant posture.

Preoccupation or distraction may increase low levels of fatigue. Preoccupation and distracted driving may be more detrimental as fatigue increases. Detection may be based on continuous driver assessment and reduced good-driver behaviors such as frequency of checking mirrors, speed control, keeping a safe distance from other vehicles, and recognizing changes in the driving environment. Through attentiveness management using hardware and software mentioned, as well as gamification, metrics (objective and measurable units to determine quality of driving), and coaching (suggestions on how to better perform as a driver) are provided to the occupant-driver. Early fatigue or lower attentiveness may be minimized.

A prediction algorithm may quantify and map different input parameters to an output of occupant fatigue levels. Different fatigue mitigation methods and therapies may be developed along the fatigue accumulation timeline before and during a trip. Data collected from large numbers of drivers may help identify high-risk roads to add signs, make changes to infrastructure, provide mitigation actions, and issue in-cabin alerts.

FIG. 24 provides an overview of an algorithm showing a combination result. The combination results in an individual profile that provides an intersection of data not otherwise known. Sleep data, chronic sleep debt, number of hours awake per day, alertness through each day, circadian rhythm patterns, a work load factor, vehicle CO2 concentration, vehicle light level and color, sitting posture, vehicle noise, vehicle vibration, and related biometrics of an individual may all feed into defining an in-vehicle fatigue-prediction model.

The related determination factors for the model of FIG. 24 may include effectiveness, a mean cognitive level, a lapse index, estimated reaction time of the individual, and a reservoir to determine remaining energy levels. As a result, the fatigue-prediction system may determine driver awareness, when and how a high-risk alert should be implemented, one or more recommendations for the individual, adaptive cabin mechanisms within the vehicle to minimize fatigue (for example, automatic climate control and music system control), and long-term drive planning.

FIG. 25 provides an overview of low-fatigue, mild-fatigue, and high-fatigue (impairment) zones. The system may minimize impairment and maximize the time of the individual within the low-fatigue zone.

Extending the low-fatigue zone of the fatigue meter may be a desired outcome of the fatigue prediction system. Managing the fatigue in advance may be more effective than reactive fatigue solutions. Extending the low-fatigue zone of the fatigue meter may be achieved by greater accuracy in estimating an occupant-driver fatigue level over time, applying and observing different therapies that may be mild or pleasing to the occupant-driver (such as music, light, massage, dynamic support, etc.) or more intrusive warnings (such as bright lights or assertive haptic vibrations, etc.), and CO2 concentration monitoring and management in the cabin.

In one embodiment of fatigue monitoring mode, there is fatigue prediction, route planning, and biometric monitoring. Reference is hereby made to U.S. Patent Application Publication No. 2015/0313475 filed May 18, 2015 and titled VEHICLE SEAT WITH INTEGRATED SENSORS for disclosure relating to use of sensors to obtain biometric data about an occupant, which application is hereby incorporated in its entirety herein. Fatigue minimization mode may trigger one or more different mild therapies, while the machine learns the relationship between the therapies and beneficial bio-feedback. The methods of therapy and stimulation to increase the low-fatigue zone may improve over time and may adjust to each individual's feedback. Fatigue mitigation mode may trigger more invasive therapies as well as predict and detect the onset of drowsiness. Under the high-fatigue, or impairment zone, there may be a stop mechanism available to the individual in which there is a high-risk warning. Auto-pilot overriding the driver may be engaged under abnormal operation by the driver and suggestions to pull over and take a break (or other action) may be engaged.

A tailored fatigue mitigation strategy may be learned by the system and a more effective strategy may be used for each individual profile. An estimate of the occupant-driver's fatigue level can be determined and the individual can be informed prior to experiencing the impact of fatigue or drowsiness. If the system detects a risk of falling asleep, the system may recommend a break. The system may engage only for accident avoidance, and may simply cause a delay to minimize current or near-term driver incapacitation.

In the case of semi-autonomous vehicles, prediction provides a vehicle time to interact with the occupant-driver in subtle and incremental ways. For example, based on the occupant's fatigue level, the vehicle may adjust to compensate for greater or less time to engage in driver hand-over for a semi-autonomous scenario.

Alertness is desired and sleep may be avoided or discouraged through the application of therapies. If the system determines the driver may be unfit for full manual control of the vehicle, the vehicle may remain under semi-autonomous control. The fatigue prediction may inform the dominant-driver over-ride level of ADAS.

The higher the fatigue level, the more support to drivers may be provided by the system. Also, a higher number and urgency level of alerts are provided from the associated ADAS. Fatigue prediction may help determine risk level in advance and give the driver more time to take control before an auto pull-over operation is triggered based on severe or prolonged drowsiness detection.

Reference is hereby made to U.S. application Ser. No. 15/692,396 filed Aug. 31, 2017 and titled VEHICLE SEAT for disclosure relating to use of topics, which application is hereby incorporated in its entirety herein. In illustrative embodiments using the ACTIVE WELLNESS™ experience, as shown in FIGS. 1 and 9, a learning protocol may be engaged to automate determination of the occupant status. The occupant status may be used to determine probable occupant motion sickness, stress, comfort level, apparent vigilance, and drowsiness level. The plurality of sensors provides data collection in order to determine occupant status in the learning protocol for use in the improvement protocol. The improvement protocol may comprise adjustment of one or more parts of the seat, one or more massage programs with adjustable intensities, adjustment of seat ventilation, adjustment of cabin ventilation, adjustment of seat and/or cabin temperature, adjustment of lighting via color, location, and intensity with respect to the occupant, adjustment of audible cues and/or music, and adjustment of air quality.

Relevant sensor data streams and displays may be provided when there is comfort rejuvenation needed prior to the occupant-driver becoming drowsy. This may be due to fatigue levels of the occupant or lack of motion detected while the occupant is positioned in the vehicle seat.

It may be too late to take effective measures to mitigate fatigue or drowsiness when drowsiness signs easily detectable and have already overtaken drivers. In illustrative embodiments, occupant fatigue may be predicted. Driver fatigue may have the similar effects as alcohol and drugs on safe driving, affecting reaction time, lapse likelihood, cognitive effectiveness, etc. Driver fatigue may be difficult to predict and drivers themselves may not know or be aware of their fatigue levels. This disclosure may apply equally to all vehicles, including but not limited to plant and machine operators, industrial workers, airlines, and other places of employment for staff fatigue management.

The following numbered clauses include embodiments that are contemplate and non-limiting:

Clause 1. An occupant support system for use in a vehicle, the occupant support comprising a sensor system configured to obtain biometrics input associated with physiological and behavioral characteristics of an occupant of the occupant support system.

Clause 2. The occupant support system of clause 1, any other clause, or any combination of clauses, wherein the sensor system is configured to obtain sleep input associated with sleep characteristics of the occupant.

Clause 3. The occupant support system of clause 2, any other clause, or any combination of clauses, wherein the sensor system is configured to obtain vehicle input associated with characteristics of the vehicle and environment surrounding the vehicle.

Clause 4. The occupant support system of clause 3, any other clause, or any combination of clauses, further comprising a control system configured to receive the biometrics input, sleep input, and vehicle input.

Clause 5. The occupant support system of clause 4, any other clause, or any combination of clauses, wherein the control system is configured to determine a biometrics score based on the biometrics input, determine a sleep score based on the sleep input, determine a task score based on the vehicle input.

Clause 6. The occupant support system of clause 5, any other clause, or any combination of clauses, wherein the control system is configured to determine occupant fatigue based on the biometrics score, the sleep score, and the task score.

Clause 7. The occupant support system of clause 6, any other clause, or any combination of clauses, wherein the control system is configured to activate a vehicle system based on the occupant fatigue.

Clause 8. The occupant support system of clause 7, any other clause, or any combination of clauses, wherein the sleep input includes a number of hours that the occupant has been without sleep, a sleep history, and circadian information.

Clause 9. The occupant support system of clause 7, any other clause, or any combination of clauses, wherein the vehicle input includes traffic information, a level of carbon dioxide in a cabin of the vehicle, a light level in the cabin of the vehicle, a noise level in the cabin, and vibration of the occupant support.

Clause 10. The occupant support system of clause 7, any other clause, or any combination of clauses, wherein the biometrics input includes heart rate of the occupant, a respiration rate of the occupant, an eye blink rate of the occupant, a head position of the occupant, and a posture of the occupant.

Clause 11. The occupant support system of clause 7, any other clause, or any combination of clauses, wherein the control system is configured to identify the occupant based on at least one of input from the occupant and the biometrics input Clause 12. The occupant support system of clause 11, any other clause, or any combination of clauses, wherein the control system is configured to associate the biometrics input, sleep input, and task input with a unique occupant data profile for the occupant.

Clause 13. The occupant support system of clause 12, any other clause, or any combination of clauses, wherein the control system is further configured to receive supplemental biometrics input after activating the vehicle system, determine a supplemental biometrics score based on the supplemental biometrics input, and determine occupant fatigue based on the supplemental biometrics score, the sleep score, and the task score.

Clause 14. The occupant support system of clause 13, any other clause, or any combination of clauses, wherein the control system is further configured to compare the biometrics score and the supplemental biometrics score and associate changes to the biometrics score in the unique occupant data profile.

Clause 15. The occupant support system of clause 7, any other clause, or any combination of clauses, wherein activating the vehicle system includes generating and displaying a suggested travel route to the occupant.

Clause 16. The occupant support system of clause 7, any other clause, or any combination of clauses, wherein activating the vehicle system includes changing the vehicle from manual operation to autonomous operation.

Clause 17. The occupant support system of clause 7, any other clause, or any combination of clauses, wherein the biometrics input includes information indicative of a respiration rate of the occupant included in signals received from a piezoelectric sensor and an electrode included in the sensor system, a posture of the occupant included in signals received from a load cell and an optical camera included in the sensor system, an eye gaze of the occupant included in signals received from the optical camera, and a head tilt of the occupant included in signals received from the optical camera.

Clause 18. The occupant support system of clause 7, any other clause, or any combination of clauses, wherein the biometrics input includes information indicative of a humidity around the occupant included in signals received from a humidity sensor included in the sensor system, an eye closure of the occupant included in signals received from an optical camera included in the sensor system, an eye blink rate of the occupant included in signals received from the optical camera, a yawn rate of the occupant included in signals received from the optical camera, and a breathing rate of the occupant included in signals received from a piezoelectric sensor and an electrode included in the sensor system.

Clause 19. The occupant support system of clause 7, any other clause, or any combination of clauses, wherein the biometrics input includes information indicative of an eye closure level of the occupant, an eye blink rate of the occupant, a yawn rate of the occupant, and a head tilt of the occupant, each included in signals received from an optical camera included in the sensor system.

Clause 20. The occupant support system of clause 7, any other clause, or any combination of clauses, wherein each of the biometrics score, sleep score, and task score are rated on a three-level scale.

Clause 21. An occupant support system for use in a vehicle, the occupant support comprising a sensor system configured to obtain biometrics input, sleep input, and vehicle input.

Clause 22. The occupant support system of clause 21, any other clause, or any combination of clauses, further comprising a control system configured to receive the biometrics input, the sleep input, and the vehicle input.

Clause 23. The occupant support system of clause 22, any other clause, or any combination of clauses, wherein the control system is configured to determine a biometrics score based on the biometrics input, determine a sleep score based on the sleep input, and determine a task score based on the vehicle input.

Clause 24. The occupant support system of clause 23, any other clause, or any combination of clauses, wherein the control system is configured to determine occupant fatigue based on the biometrics score, sleep score, and the task score.

Clause 25. The occupant support system of clause 24, any other clause, or any combination of clauses, wherein the control system is configured to change between a fatigue monitoring mode, a fatigue prevention mode, a fatigue mitigation mode, a warning mode, and a stop mode based on the determined occupant fatigue.

Clause 26. The occupant support system of clause 25, any other clause, or any combination of clauses, wherein the control system generates a suggested travel route in the fatigue monitoring mode.

Clause 27. The occupant support system of clause 25, any other clause, or any combination of clauses, wherein the control system is configured to activate at least one of a massage system, a sound system, a light system, and an aroma system included in the vehicle in the fatigue prevention mode.

Clause 28. The occupant support system of clause 27, any other clause, or any combination of clauses, wherein the control system is further configured to receive supplemental biometrics input after activating the at least one of the massage system, the sound system, the light system, and the aroma system, determine a supplemental biometrics score based on the supplemental biometrics input, and determine occupant fatigue based on the supplemental biometrics score, the sleep score, and the task score.

Clause 29. The occupant support system of clause 25, any other clause, or any combination of clauses, wherein the control system generates a warning signal in the warning mode.

Clause 30. The occupant support system of clause 25, any other clause, or any combination of clauses, wherein the control system generates a stop signal in the stop mode and the stop signal is configured to change the vehicle from manual operation to autonomous operation or to stop the vehicle.

Clause 31. The occupant support system of clause 25, any other clause, or any combination of clauses, wherein the control system is configured to identify the occupant based on at least one of input from the occupant and the biometrics input.

Clause 32. The occupant support system of clause 31, any other clause, or any combination of clauses, wherein the control system is configured to associate the biometrics input, sleep input, and task input with a unique occupant data profile for the occupant.

The invention claimed is:

1. An occupant support system for use in a vehicle, the occupant support comprising
   a sensor system configured to obtain biometrics input associated with physiological and behavioral characteristics of an occupant of the occupant support system, sleep input associated with sleep characteristics of the occupant, and vehicle input associated with characteristics of the vehicle and environment surrounding the vehicle, and
   a control system configured to receive the biometrics input, sleep input, and vehicle input, determine a biometrics score based on the biometrics input, determine a sleep score based on the sleep input, determine a task score based on the vehicle input, determine occupant fatigue based on the biometrics score, the sleep score, and the task score, and activate a vehicle system based on the occupant fatigue,
   wherein the control system is further configured to identify the occupant based on at least one of input from the occupant and the biometrics input and to associate the biometrics input, sleep input, and task input with a unique occupant data profile for the occupant,
   wherein the control system is further configured to receive supplemental biometrics input after activating the vehicle system, determine a supplemental biometrics score based on the supplemental biometrics input, and determine occupant fatigue based on the supplemental biometrics score, the sleep score, and the task score.

2. The occupant support system of claim 1, wherein the sleep input includes a number of hours that the occupant has been without sleep, a sleep history, and circadian information.

3. The occupant support system of claim 2, wherein the vehicle input includes traffic information, a level of carbon dioxide in a cabin of the vehicle, a light level in the cabin of the vehicle, a noise level in the cabin, and vibration of the occupant support.

4. The occupant support system of claim 3, wherein the biometrics input includes heart rate of the occupant, a respiration rate of the occupant, an eye blink rate of the occupant, a head position of the occupant, and a posture of the occupant.

5. The occupant support system of claim 1, wherein the control system is further configured to compare the biometrics score and the supplemental biometrics score and associate changes to the biometrics score in the unique occupant data profile.

6. The occupant support system of claim 1, wherein activating the vehicle system includes generating and displaying a suggested travel route to the occupant.

7. The occupant support system of claim 1, wherein activating the vehicle system includes changing the vehicle from manual operation to autonomous operation.

8. The occupant support system of claim 1, wherein the biometrics input includes information indicative of a respiration rate of the occupant included in signals received from a piezoelectric sensor and an electrode included in the sensor system, a posture of the occupant included in signals received from a load cell and an optical camera included in the sensor system, an eye gaze of the occupant included in signals received from the optical camera, and a head tilt of the occupant included in signals received from the optical camera.

9. The occupant support system of claim 1, wherein the biometrics input includes information indicative of a humidity around the occupant included in signals received from a humidity sensor included in the sensor system, an eye closure of the occupant included in signals received from an optical camera included in the sensor system, an eye blink rate of the occupant included in signals received from the optical camera, a yawn rate of the occupant included in signals received from the optical camera, and a breathing rate of the occupant included in signals received from a piezoelectric sensor and an electrode included in the sensor system.

10. The occupant support system of claim 1, wherein the biometrics input includes information indicative of an eye closure level of the occupant, an eye blink rate of the occupant, a yawn rate of the occupant, and a head tilt of the occupant, each included in signals received from an optical camera included in the sensor system.

11. An occupant support system for use in a vehicle, the occupant support comprising
a sensor system configured to obtain biometrics input associated with physiological and behavioral characteristics of an occupant of the occupant support system, sleep input associated with sleep characteristics of the occupant, and vehicle input associated with characteristics of the vehicle and environment surrounding the vehicle, and
a control system configured to receive the biometrics input, sleep input, and vehicle input, determine a biometrics score based on the biometrics input, determine a sleep score based on the sleep input, determine a task score based on the vehicle input, determine occupant fatigue based on the biometrics score, the sleep score, and the task score, and activate a vehicle system based on the occupant fatigue,
wherein the control system further configured to rate each of the biometrics score, sleep score, and task score on a three-level scale.

12. An occupant support system for use in a vehicle, the occupant support comprising
a sensor system configured to obtain biometrics input of an occupant of the occupant support system, sleep input of the occupant support system, and vehicle input, and
a control system configured to receive the biometrics input, the sleep input, and the vehicle input, determine a biometrics score based on the biometrics input, determine a sleep score based on the sleep input, determine a task score based on the vehicle input, determine occupant fatigue based on the biometrics score, sleep score, and the task score, and change between a fatigue monitoring mode, a fatigue prevention mode, a fatigue mitigation mode, a warning mode, and a stop mode based on the determined occupant fatigue,
wherein the control system is configured to activate at least one of a massage system, a sound system, a light system, and an aroma system included in the vehicle in the fatigue prevention mode,
wherein the control system is further configured to receive supplemental biometrics input after activating the at least one of the massage system, the sound system, the light system, and the aroma system, determine a supplemental biometrics score based on the supplemental biometrics input, and determine occupant fatigue based on the supplemental biometrics score, the sleep score, and the task score.

13. The occupant support system of claim 12, wherein the control system generates a suggested travel route in the fatigue monitoring mode.

14. The occupant support system of claim 12, wherein the control system generates a warning signal in the warning mode.

15. The occupant support system of claim 12, wherein the control system generates a stop signal in the stop mode and the stop signal is configured to change the vehicle from manual operation to autonomous operation or to stop the vehicle.

16. The occupant support system of claim 12, wherein the control system is further configured to identify the occupant based on at least one of input from the occupant and the biometrics input and to associate the biometrics input, sleep input, and task input with a unique occupant data profile for the occupant.

* * * * *